US009314600B2

(12) United States Patent
Paris et al.

(10) Patent No.: US 9,314,600 B2
(45) Date of Patent: Apr. 19, 2016

(54) DELIVERY SYSTEM FOR IMPLANTABLE FLOW CONNECTOR

(71) Applicant: Bioconnect Systems, Inc., Fort Washington, PA (US)

(72) Inventors: Michael Paris, Lansdale, PA (US); Adam Dakin, Jr., Fort Washington, PA (US); Todd Polk, Doylestown, PA (US); Mahesh Krishnamoorthy, Lansdale, PA (US); Stephen Paris, Campbell Hall, NY (US)

(73) Assignee: Bioconnect Systems, Inc., Fort Washington, PA (US)

( * ) Notice: Subject to any disclaimer, the term of this patent is extended or adjusted under 35 U.S.C. 154(b) by 367 days.

(21) Appl. No.: 13/798,831

(22) Filed: Mar. 13, 2013

(65) Prior Publication Data
US 2013/0274646 A1    Oct. 17, 2013

Related U.S. Application Data

(60) Provisional application No. 61/624,390, filed on Apr. 15, 2012.

(51) Int. Cl.
| *A61M 5/00* | (2006.01) |
| *A61M 27/00* | (2006.01) |
| *A61F 2/06* | (2013.01) |
| *A61B 17/11* | (2006.01) |
| *A61F 2/966* | (2013.01) |
| *A61B 17/00* | (2006.01) |
| *A61F 2/95* | (2013.01) |

(52) U.S. Cl.
CPC ............. *A61M 27/002* (2013.01); *A61B 17/11* (2013.01); *A61F 2/064* (2013.01); *A61F 2/966* (2013.01); *A61B 2017/00424* (2013.01); *A61B 2017/1107* (2013.01); *A61B 2017/1135* (2013.01); *A61F 2002/9522* (2013.01)

(58) Field of Classification Search
CPC ........... A61B 17/11; A61B 2017/1107; A61B 17/0057; A61B 2017/1139; A61B 2017/1135; A61B 2017/00367; A61B 2017/00592; A61B 2017/00632; A61B 2017/068; A61M 27/00; A61M 37/0069
USPC ............................................................ 604/8
See application file for complete search history.

(56) References Cited

U.S. PATENT DOCUMENTS

| 2,127,903 | A |   | 8/1938 | Bowen |
| 2,620,061 | A | * | 12/1952 | Uxa ...................... A24F 15/16 |
|           |   |   |         | 221/229 |
| 3,974,835 | A |   | 8/1976 | Hardy, Jr. |

(Continued)

FOREIGN PATENT DOCUMENTS

| JP | 02003220065 | 8/2003 |
| WO | WO 98/19629 | 5/1998 |

(Continued)

*Primary Examiner* — Tatyana Zalukaeva
*Assistant Examiner* — Ariana Zimbouski

(57) ABSTRACT

A delivery system for delivering an implant to a first space within a body of a patient including an elongate delivery member having a proximal portion, a distal portion, a lumen and a receiving area, the receiving area dimensioned for receipt of the implant. A deforming member is movable with respect to the delivery member from a first position to a second position to apply a force to the implant to deform the implant positioned in the receiving area of the delivery member.

4 Claims, 24 Drawing Sheets

(56) References Cited

U.S. PATENT DOCUMENTS

| | | | |
|---|---|---|---|
| 4,352,358 | A | 10/1982 | Angelchik |
| 4,451,254 | A * | 5/1984 | Dinius .............. A61M 37/0069 206/535 |
| 4,667,673 | A | 5/1987 | Li |
| 4,705,040 | A | 11/1987 | Mueller et al. |
| 4,787,386 | A | 11/1988 | Walsh et al. |
| 5,141,516 | A | 8/1992 | Detweiler |
| 5,453,090 | A | 9/1995 | Martinez et al. |
| 5,456,714 | A | 10/1995 | Owen |
| 5,503,635 | A | 4/1996 | Sauer et al. |
| 5,586,987 | A | 12/1996 | Fahy |
| 5,634,936 | A | 6/1997 | Linden et al. |
| 5,669,924 | A | 9/1997 | Shaknovich |
| 5,676,670 | A | 10/1997 | Kim |
| 5,683,451 | A | 11/1997 | Lenker et al. |
| 5,716,325 | A | 2/1998 | Bonutti |
| 5,830,222 | A | 11/1998 | Makower |
| 5,853,422 | A | 12/1998 | Huebsch et al. |
| 5,868,761 | A | 2/1999 | Nicholas et al. |
| 5,868,763 | A | 2/1999 | Spence et al. |
| 5,868,777 | A | 2/1999 | Lam |
| 5,893,886 | A | 4/1999 | Zegdi et al. |
| 5,976,178 | A | 11/1999 | Goldsteen et al. |
| 6,017,352 | A | 1/2000 | Nash et al. |
| 6,030,395 | A | 2/2000 | Nash et al. |
| 6,036,702 | A | 3/2000 | Bachinski et al. |
| 6,036,705 | A | 3/2000 | Nash et al. |
| 6,056,762 | A | 5/2000 | Nash et al. |
| 6,063,114 | A | 5/2000 | Nash et al. |
| 6,068,638 | A | 5/2000 | Makower |
| 6,113,612 | A | 9/2000 | Swanson et al. |
| 6,152,945 | A | 11/2000 | Bachinski et al. |
| 6,165,185 | A | 12/2000 | Shennib et al. |
| 6,176,864 | B1 | 1/2001 | Chapman |
| 6,190,353 | B1 | 2/2001 | Makower et al. |
| 6,190,397 | B1 | 2/2001 | Spence et al. |
| 6,193,734 | B1 | 2/2001 | Bolduc et al. |
| 6,206,913 | B1 | 3/2001 | Yencho et al. |
| 6,214,022 | B1 | 4/2001 | Taylor et al. |
| 6,217,585 | B1 | 4/2001 | Houser et al. |
| 6,231,587 | B1 | 5/2001 | Makower |
| 6,241,741 | B1 | 6/2001 | Duhaylongsod et al. |
| 6,251,116 | B1 | 6/2001 | Shennib et al. |
| 6,283,983 | B1 | 9/2001 | Makower et al. |
| 6,302,905 | B1 | 10/2001 | Goldsteen et al. |
| 6,350,280 | B1 | 2/2002 | Nash et al. |
| 6,371,965 | B2 | 4/2002 | Gifford, III et al. |
| 6,402,767 | B1 | 6/2002 | Nash et al. |
| 6,409,739 | B1 | 6/2002 | Nobles et al. |
| 6,419,681 | B1 | 7/2002 | Vargas et al. |
| 6,428,550 | B1 | 8/2002 | Vargas et al. |
| 6,440,163 | B1 | 8/2002 | Swanson et al. |
| 6,443,965 | B1 | 9/2002 | Gifford, III et al. |
| 6,458,140 | B2 | 10/2002 | Akin et al. |
| 6,461,320 | B1 | 10/2002 | Yencho et al. |
| 6,464,709 | B1 | 10/2002 | Shennib et al. |
| 6,485,496 | B1 | 11/2002 | Suyker et al. |
| 6,497,710 | B2 | 12/2002 | Yencho et al. |
| 6,508,824 | B1 | 1/2003 | Flaherty et al. |
| 6,517,558 | B2 | 2/2003 | Gittings et al. |
| 6,537,287 | B1 | 3/2003 | Yencho et al. |
| 6,537,288 | B2 | 3/2003 | Vargas et al. |
| 6,565,581 | B1 | 5/2003 | Spence et al. |
| 6,585,762 | B1 | 7/2003 | Stanish |
| 6,616,675 | B1 | 9/2003 | Evard et al. |
| 6,620,129 | B2 | 9/2003 | Stecker et al. |
| 6,626,920 | B2 | 9/2003 | Whayne |
| 6,648,901 | B2 | 11/2003 | Fleischman et al. |
| 6,652,543 | B2 | 11/2003 | Spence et al. |
| 6,655,386 | B1 | 12/2003 | Makower et al. |
| 6,699,257 | B2 | 3/2004 | Gifford, III et al. |
| 6,709,441 | B2 | 3/2004 | Bolduc et al. |
| 6,719,781 | B1 | 4/2004 | Kim |
| 6,726,697 | B2 | 4/2004 | Nicholas et al. |
| 6,736,825 | B2 | 5/2004 | Blatter et al. |
| 6,740,101 | B2 | 5/2004 | Houser et al. |
| 6,776,785 | B1 | 8/2004 | Yencho et al. |
| 6,786,914 | B1 | 9/2004 | Vargas et al. |
| 6,790,229 | B1 | 9/2004 | Berreklouw |
| 6,913,607 | B2 | 7/2005 | Ainsworth et al. |
| 6,916,327 | B2 | 7/2005 | Northrup, III et al. |
| 6,926,724 | B1 | 8/2005 | Chu |
| 6,962,596 | B2 | 11/2005 | Bolduc et al. |
| 6,972,023 | B2 | 12/2005 | Whayne et al. |
| 7,008,436 | B2 | 3/2006 | Barath |
| 7,018,388 | B2 | 3/2006 | Yencho et al. |
| 7,025,773 | B2 | 4/2006 | Gittings et al. |
| 7,029,482 | B1 | 4/2006 | Vargas et al. |
| 7,041,110 | B2 | 5/2006 | Yencho et al. |
| 7,063,711 | B1 * | 6/2006 | Loshakove et al. ........... 606/153 |
| 7,063,712 | B2 | 6/2006 | Vargas et al. |
| 7,128,749 | B1 | 10/2006 | Vargas et al. |
| 7,160,311 | B2 | 1/2007 | Blatter et al. |
| 7,172,608 | B2 | 2/2007 | Vargas et al. |
| 7,175,637 | B2 | 2/2007 | Vargas et al. |
| 7,351,247 | B2 | 4/2008 | Kupiecki et al. |
| 7,892,246 | B2 | 2/2011 | Akin et al. |
| 7,892,247 | B2 | 2/2011 | Conston et al. |
| 8,366,651 | B2 | 2/2013 | Dakin et al. |
| 2001/0047165 | A1 | 11/2001 | Makower et al. |
| 2002/0022853 | A1 | 2/2002 | Swanson et al. |
| 2002/0029079 | A1 | 3/2002 | Kim et al. |
| 2002/0091398 | A1 | 7/2002 | Galdonik et al. |
| 2003/0065344 | A1 | 4/2003 | Kirsch et al. |
| 2003/0100920 | A1 | 5/2003 | Akin et al. |
| 2003/0212418 | A1 | 11/2003 | Yencho et al. |
| 2003/0225425 | A1 | 12/2003 | Kupiecki et al. |
| 2003/0229365 | A1 | 12/2003 | Whayne et al. |
| 2003/0236542 | A1 | 12/2003 | Makower |
| 2004/0073238 | A1 | 4/2004 | Makower |
| 2004/0073282 | A1 | 4/2004 | Stanish |
| 2004/0087984 | A1 * | 5/2004 | Kupiecki et al. .............. 606/153 |
| 2004/0088042 | A1 | 5/2004 | Kim et al. |
| 2004/0097991 | A1 | 5/2004 | Vargas et al. |
| 2004/0102796 | A1 | 5/2004 | Hill et al. |
| 2004/0122318 | A1 | 6/2004 | Flaherty et al. |
| 2004/0132225 | A1 | 7/2004 | ***Chung |
| 2004/0158143 | A1 | 8/2004 | Flaherty et al. |
| 2004/0249400 | A1 | 12/2004 | Vargas et al. |
| 2005/0043751 | A1 | 2/2005 | Phan et al. |
| 2005/0043752 | A1 | 2/2005 | Phan et al. |
| 2005/0149073 | A1 | 7/2005 | Arani et al. |
| 2006/0064119 | A9 | 3/2006 | Tilson et al. |
| 2006/0161265 | A1 | 7/2006 | Levine et al. |
| 2006/0241342 | A1 | 10/2006 | Macaulay et al. |
| 2007/0027526 | A1 | 2/2007 | Demetriades |
| 2008/0109069 | A1 | 5/2008 | Coleman et al. |
| 2009/0036820 | A1 * | 2/2009 | Dakin .................... A61B 17/11 604/9 |
| 2012/0065652 | A1 | 3/2012 | Cully et al. |
| 2012/0071965 | A1 | 3/2012 | Longo et al. |
| 2013/0197546 | A1 | 8/2013 | Paris et al. |

FOREIGN PATENT DOCUMENTS

| | | |
|---|---|---|
| WO | WO 98/19635 | 5/1998 |
| WO | WO 98/52474 | 11/1998 |
| WO | WO 99/11180 | 3/1999 |
| WO | WO 00/27310 | 5/2000 |
| WO | WO 00/27313 | 5/2000 |
| WO | WO 00/53104 | 9/2000 |
| WO | WO 01/39672 | 6/2001 |
| WO | WO 2011/020099 | 2/2011 |

* cited by examiner

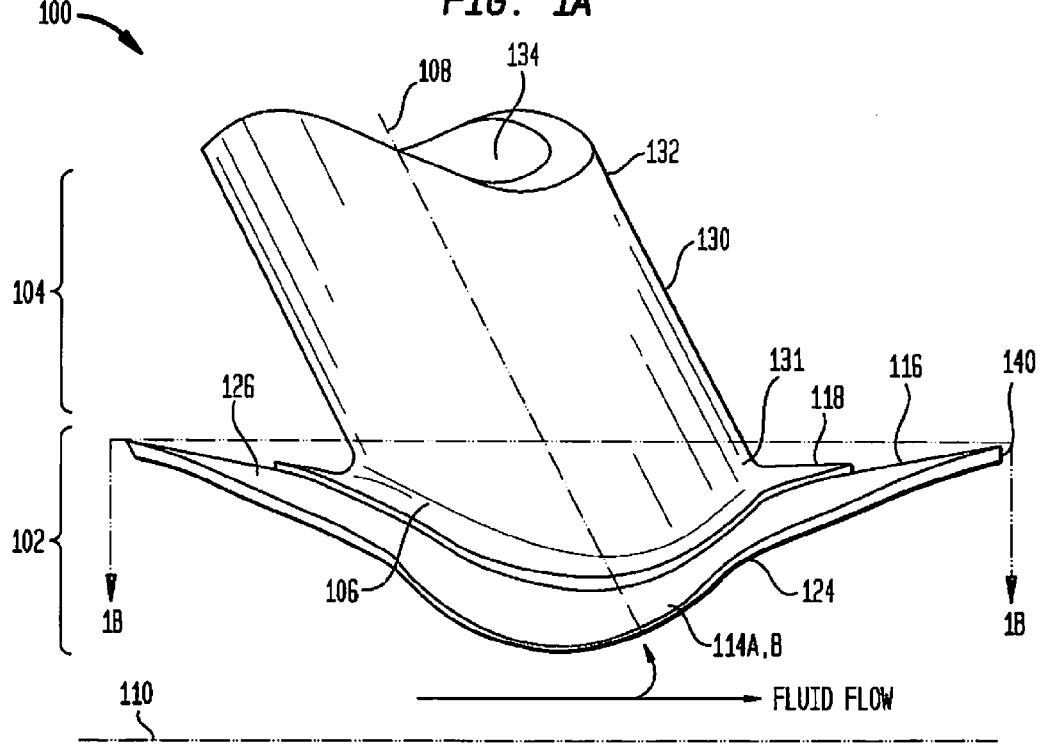
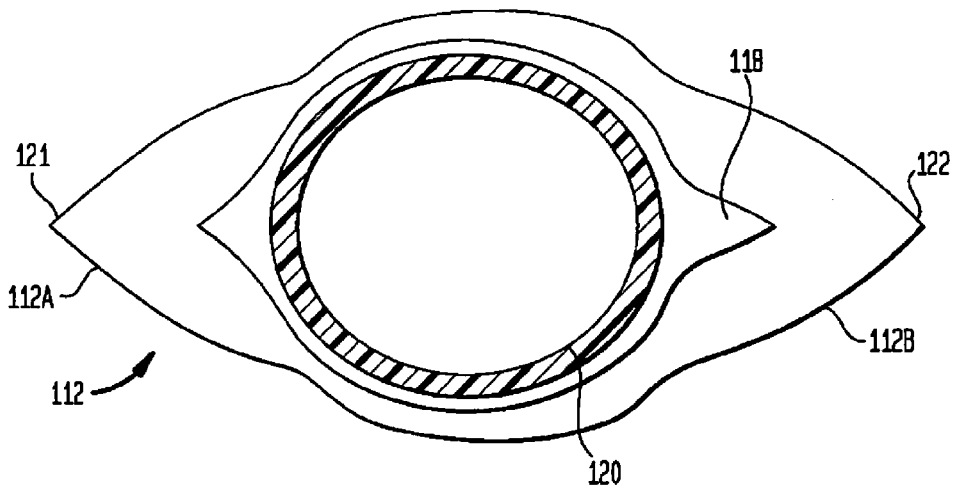

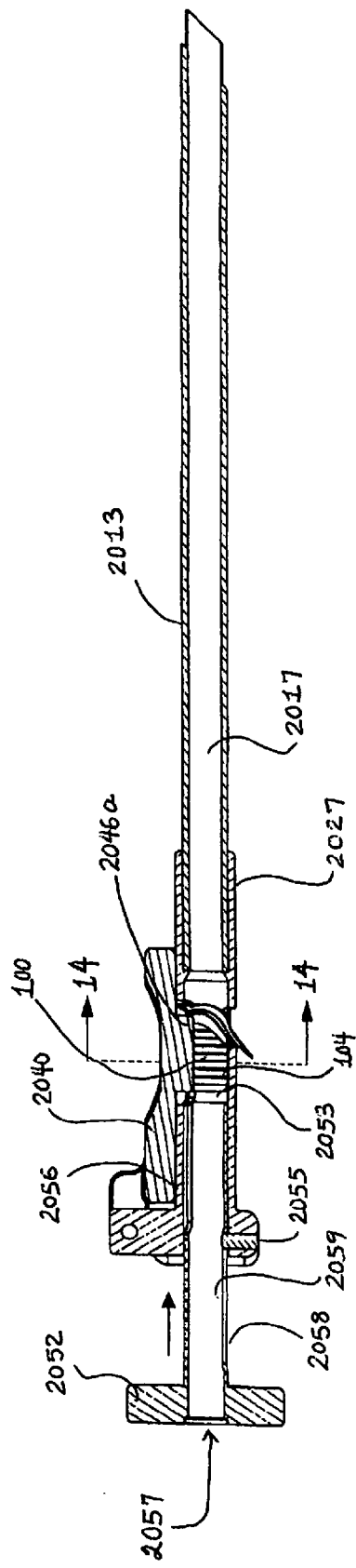
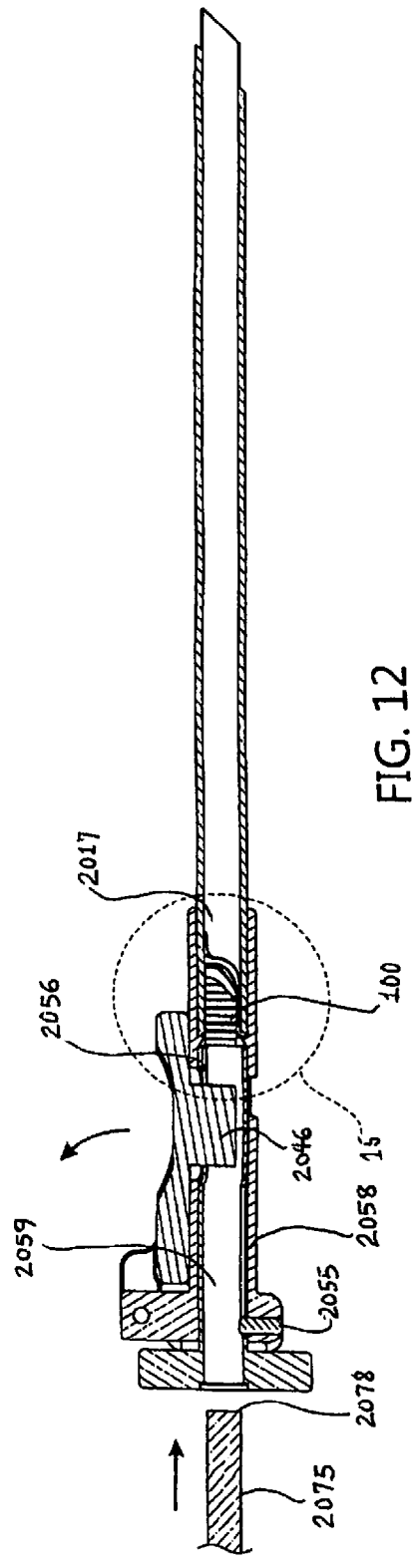
FIG. 11
FIG. 12

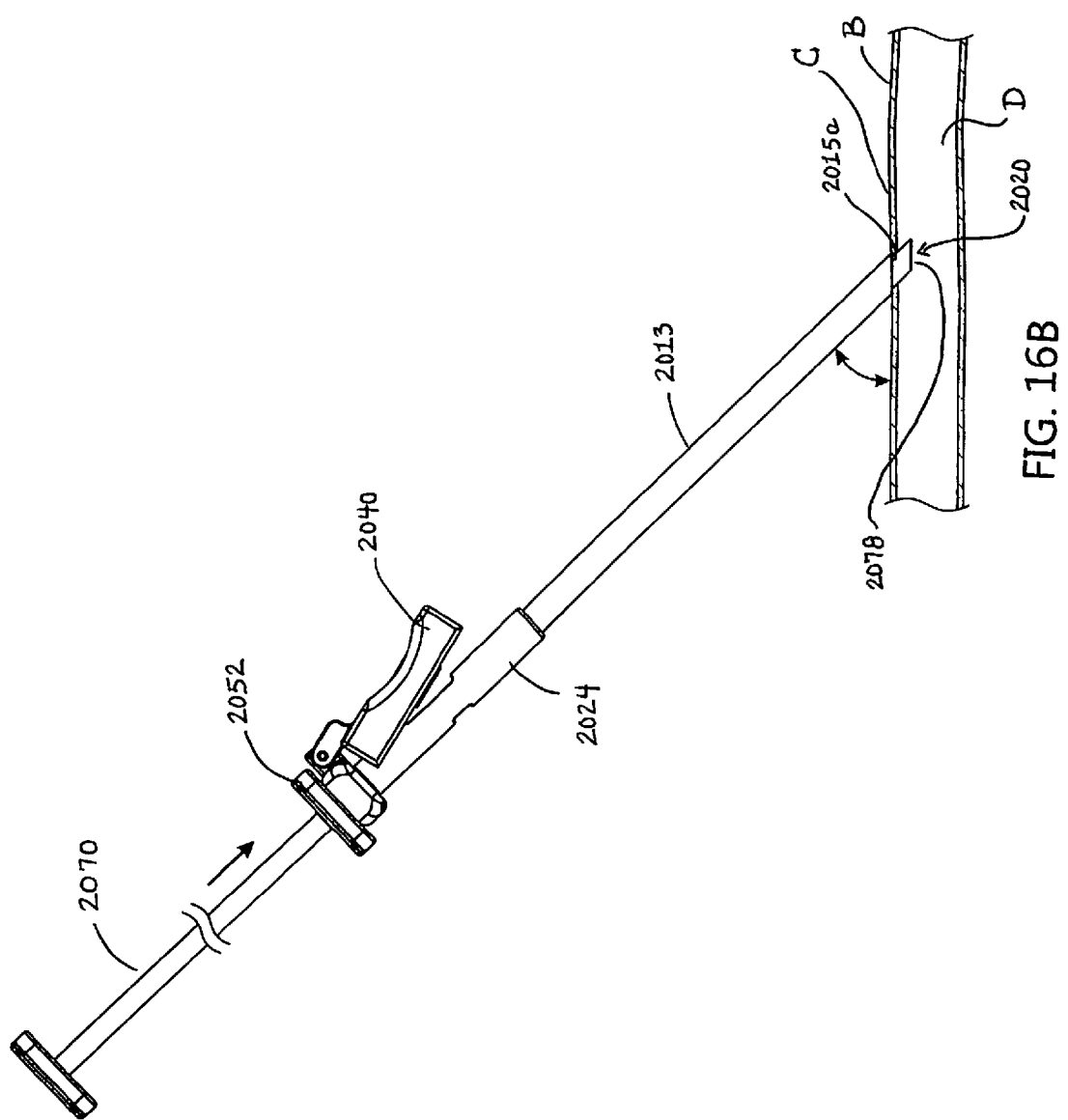

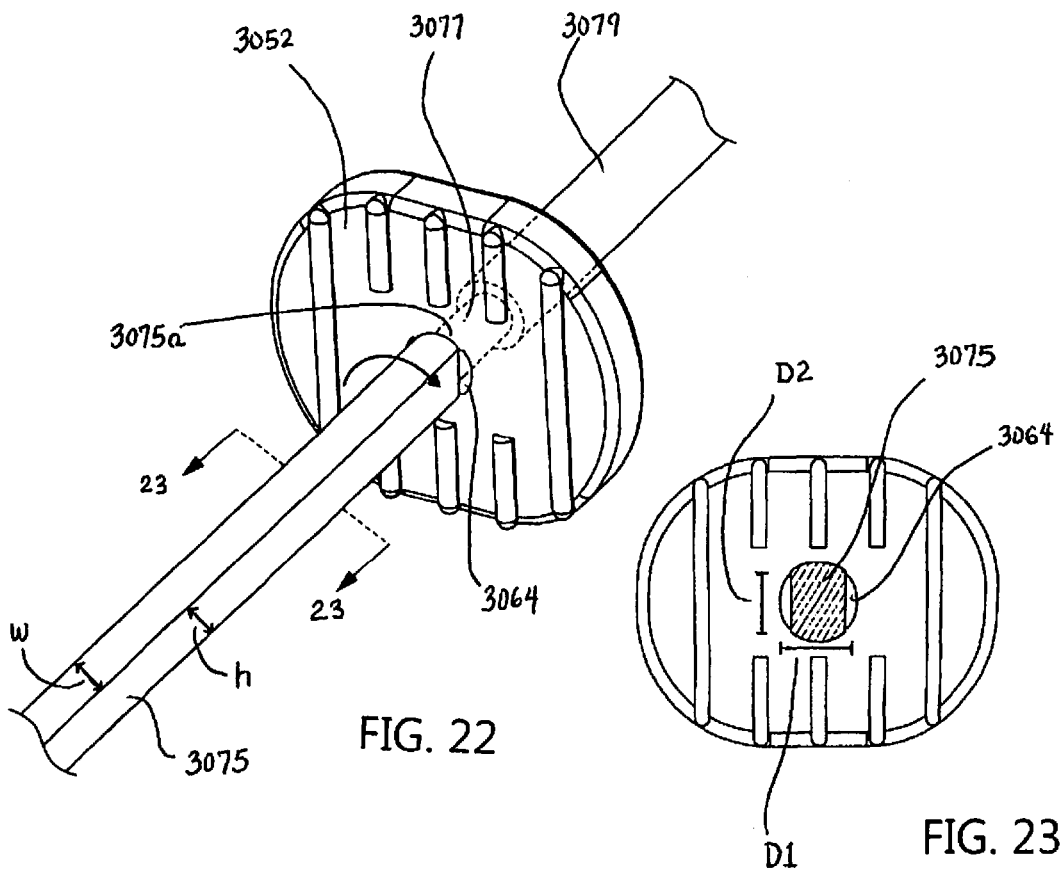
FIG. 22
FIG. 23
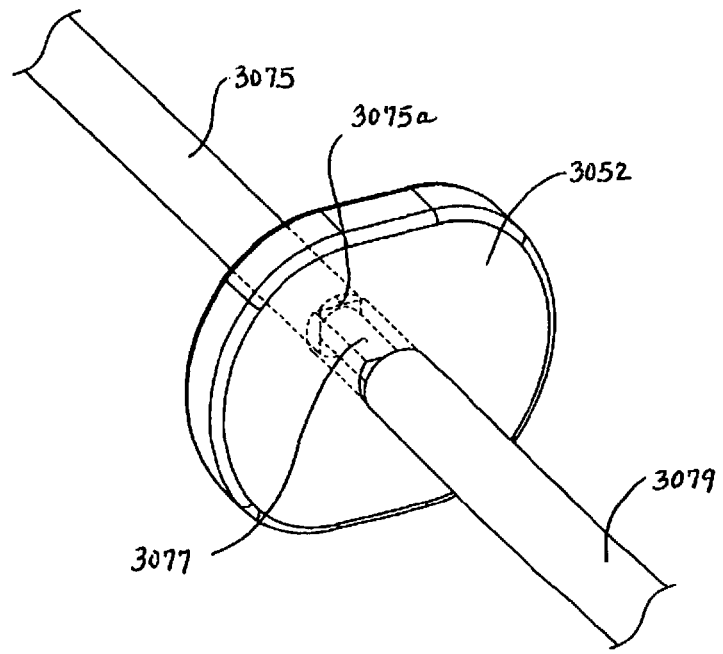
FIG. 24

DELIVERY SYSTEM FOR IMPLANTABLE FLOW CONNECTOR

CROSS-REFERENCE TO RELATED APPLICATIONS

This application claims the benefit of U.S. Provisional Application No. 61/624,390 filed Apr. 15, 2012, the entire contents of which are incorporated herein by reference.

BACKGROUND

1. Field of the Invention

The present invention relates generally to a delivery system for implantable medical devices and, more particularly, to delivery systems for implantable flow connectors.

2. Related Art

The mammalian body has numerous tissue-enclosed body spaces. For example, body conduits such as blood vessels, lymph and tear ducts, bowels, urethra, etc., which have a lumen through which fluid is carried to facilitate circulation, excretion or other fluid transfer function. Tissue-enclosed body spaces also include body reservoirs such as the stomach, bladder, gall bladder, lymph nodes, etc., which temporarily or permanently retain fluid.

It is often necessary or desirable to directly or indirectly connect body spaces to one another, to other areas in the body, or to an external or implantable medical device such as a sensor, pump, drug delivery system, or other permanently or temporarily implanted therapeutic device. For example, when vessels are damaged, severed or occluded due to physiological conditions, surgical intervention, or disease, certain sections of those vessels are typically bypassed to allow for the free and continuous flow of fluids. For example, an anastomosis is commonly performed for the purpose of connecting different blood vessels together to optimize or redirect blood flow around a damaged or occluded portion of a vessel or to redirect arterial flow into the venous system for enabling dialysis access.

In the context of the peripheral vascular and/or the cardiovascular system, atherosclerosis may cause partial or complete occlusion of an arterial vessel. This may result in restricted blood flow which may compromise perfusion to the tissue served by the blood flow. In the case of an occluded coronary vessel, for example, an area of the heart's myocardium would be compromised, which may lead to a myocardial infarction or other ischemic heart syndrome such as congestive heart failure. In the case of peripheral vascular atherosclerotic disease, occluded vessels lead to ischemic syndromes such as threatened limbs, stroke and other morbidities. Many cases, such a blockage or restriction in the blood flow leading to the heart or peripheral vessels, may be treated by a surgical procedure known as an artery bypass graft procedure.

A bypass procedure involves establishing an alternate blood supply path to bypass a diseased section of a diseased or compromised artery. In the bypass procedure, a surgeon typically dissects one end of a source or 'pedicled' artery (such as the internal mammary artery in the case of coronary artery bypass), or a free vessel segment (typically the saphenous vein in the leg), to use as a graft conduit to bypass the obstruction in the affected artery to restore normal blood flow. The graft vessel is connected to the obstructed vessel by means of an anastomosis procedure wherein an opening in the graft vessel is sutured to the obstructed vessel at an arteriotomy site made within the obstructed vessel. There are other indications for vessel anastomoses including revascularizing diseased arteries by creating a side-to side anastomosis between the distal end of the artery and an adjacent vein, thereby allowing the portion of the vein distal the occlusion to become "arterialized." Another indication includes arterial revascularization by "arterializing" a vein through creation of a conduit downstream of the occlusive disease.

The creation of an arteriovenous (AV) fistula is another instance where two body conduits are joined together and involves surgically joining an artery to a vein. AV fistulas are formed for a variety of reasons, one being to provide vascular access for hemodialysis patients. In such an application, the most common site for creation of the AV fistula is the upper extremity, though the lower extremity may also be used. Various surgical techniques and methods may be employed to create the AV fistula. Another indication for creation of an AV fistula is the connection of major vessels such as the aorta and the vena cava in patients with chronic obstruction pulmonary disease (COPD).

The patency of an anastomosis contributes to a successful bypass or AV fistula, both by acute and long-term evaluation. Patency may be compromised due to technical, biomechanical or pathophysiological causes. Among the technical and biomechanical causes for compromised patency are poorly achieved anastomoses due to, for example, poor technique, trauma, thrombosis, intimal hyperplasia or adverse biological responses to the anastomosis. Improperly anastomosed vessels may lead to leakage, create thrombus and/or lead to further stenosis at the communication site, possibly requiring re-operation or further intervention. As such, forming an anastomosis is a critical procedure in bypass or AV fistula surgery, requiring precision and accuracy on the part of the surgeon.

A common traditional approach for forming an anastomosis is to suture together natural or artificial openings in the vessels. To do so, according to one approach, a surgeon delicately sews the vessels together being careful not to suture too tightly so as to tear the delicate tissue, nor to suture too loosely so as to permit leakage of fluid from the anastomosis. In addition to creating a surgical field in which it is difficult to see, leakage of fluid from the anastomosis can cause serious acute or chronic complications, which may be fatal. In addition to the inherent inconsistencies in suture tightness, incision length, placement of the suture, stitch size, and reproducibility, suturing an anastomosis can be very time consuming. This difficulty is compounded by the relatively small dimensions of the vessels involved or the diseased state of the vessel when creating an AV fistula.

Implantable flow connectors for fluidly connecting body spaces are disclosed in commonly assigned U.S. Pat. No. 8,366,651 and U.S. patent publication 2009/0036820 These devices are effective in overcoming the problems and deficiencies of the prior art. Commonly assigned co-pending application Ser. No. 13/792,019, filed Mar. 9, 2013, discloses alternate embodiments wherein the flow connectors are used in conjunction with a retention device to maintain the position of the flow connector and the body spaces. The contents of each of these three applications are incorporated herein by reference in their entirety.

The need exists to provide a fast simplified way to load and deliver the forgoing flow connectors to the body space and to minimize the diameter of the delivery system. It is also desirable to provide a delivery system to deliver these flow connectors in a reliable and consistent manner.

SUMMARY

In accordance with one embodiment of the present invention, a delivery system for an implantable flow connector for fluidically coupling a source tissue-enclosed body space with a destination conduit is provided, the flow connector comprising: a conduit having a lumen having a first diameter and terminating at a first orifice at a first end of the conduit implantable in the source body space through an opening formed in a tissue wall of the source body space, and a second end of the conduit, comprising a circumferential flange, radially extending from the conduit proximate the conduit first end, configured to be implanted in the source body space adjacent an opening in the tissue wall of the source body space such that the conduit extends through the opening.

In accordance with one aspect of the present invention a delivery system for delivering an implant to a first space within a body of a patient is provided comprising an elongate delivery member having a proximal portion, a distal portion, a lumen and a receiving area, the receiving area dimensioned for receipt of the implant. A deforming member is movable with respect to the delivery member, the deforming member movable from a first position to a second position to apply a force to the implant to deform the implant positioned in the receiving area of the delivery member.

In some embodiments, the delivery member has an opening formed in a side wall, the opening communicating with the receiving area and dimensioned for insertion of the implant therethrough for placement in the receiving area of the delivery member.

In some embodiments, the deforming member is pivotably attached to the delivery member for pivotable movement between the first and second positions.

In some embodiments, the implant is a flow connector having a flange and a conduit having a lumen, wherein the deforming member contacts and deforms the conduit of the implant. The conduit can terminate at a first orifice at a first end of the conduit and a second end of the conduit can have a second orifice, and the flange can extend radially from the conduit proximate the conduit first end.

In some embodiments, the system includes a first plunger movable within the lumen of the delivery member from a proximal position to a distal position to advance the implant distally from the receiving area. In some embodiments, the first plunger can have a first lumen and the delivery system can include a second plunger insertable through the first lumen in the first plunger to advance the implant distally within the lumen of the delivery member and out of a distal opening in the delivery member. In some embodiments, the second plunger has a length greater than a length of the first plunger. In some embodiments, the first plunger has a cutout or slot to slide past the deforming member when moved to the distal position.

In some embodiments, the second plunger is slidably attached to one or both of the delivery member and first plunger; in other embodiments, the second plunger is a separate element removably insertable into the first plunger.

In some embodiments, the first plunger has a bore at a proximal end having a first dimension and a second dimension transverse to the first dimension, the second dimension being greater than the first dimension, and the second plunger has a first position to contact the first plunger to advance the first plunger and a second position to slide within the first lumen of the first plunger to advance the implant.

The outer surface of the delivery member can include a stop to limit insertion of the delivery member into the first space within the body.

The deforming member can include a folding block configured to fold the implant. In some embodiments, the implant is folded at the conduit portion without contact with the flange by the folding block.

In accordance with another aspect of the present invention, a delivery system for delivering a flow connector to a first space within a body of a patient is provided, the system comprising a flow connector, a delivery member and a deforming member. The flow connector has a conduit having a lumen with a first and second orifice, the conduit implantable in a second space within the body. The delivery member has a first opening in a side wall and a receiving area to receive the implantable flow connector inserted through the first opening in the side wall. The deforming member is movable to deform the conduit portion of the flow connector positioned in the receiving area to enable advancement of the flow connector through the delivery member in a reduced profile position.

In some embodiments, the flow connector has a flange extending radially from the conduit and configured to be implanted in the first space within the body, and the delivery member has an outer diameter and a second opening in the sidewall, and the flange is positioned in the receiving area such that the flange extends through one or both of the first and second openings such that a portion of the flange protrudes beyond the outer diameter of the delivery member. In some embodiments, as the flow connector is moved further through the delivery member, a toe portion of the flange points in a distal direction and a heel portion is alongside the conduit of the flow connector.

In accordance with another aspect of the present invention, a delivery system for delivering an implant to a first space within a body of a patient is provided, the system comprising an elongate delivery member having a proximal portion, a distal portion, a lumen and a receiving area, the receiving area dimensioned for receipt of the implant. A first plunger is movable from a first position to a second position to advance the implant from the receiving area to an intermediate position within the delivery member and a second plunger is advanceable to move the implant from the intermediate position to exit the delivery member.

The delivery system can further include a deforming member movable from a first position to a second position to deform the implant after placement within the receiving area.

In accordance with another aspect of the present invention a delivery system for delivering a flow connector to a first space within the body of a patient is provided, the system comprising an implantable flow connector and a delivery member. The flow connector has a conduit having a lumen terminating at a first orifice at a first end of the conduit implantable in the first space within the body, and a second end of the conduit has a second orifice, and a flange extends radially from the conduit proximate the conduit first end and configured to be implanted in the first space within the body. The delivery member has an outer surface, a first opening in a side wall and a receiving area to receive the implantable flow connector through the opening in the side wall, wherein when the flow connector is placed within the receiving area the flange is positioned in the receiving area such that a portion of the flange extends through the first opening in the side wall such that the portion of the flange protrudes beyond the outer surface of the delivery member.

In some embodiments, the delivery member has a second opening in a sidewall through which the flange protrudes beyond the outer surface of the delivery member.

In accordance with another aspect of the present invention, a method for delivering an implantable flow connector to a first space within the body of a patient to couple the first space within the body to a second space within the body is provided, the flow connector having a conduit with a lumen terminating at an orifice at opposing first and second ends of the conduit, wherein a second end of the conduit is configured to be implanted in the second space within the body. The method comprises the steps of: providing a delivery member having a lumen and a receiving area, placing the flow connector within the receiving area, moving a deforming member from a first position to a second position to press the conduit portion of the flow connector to deform the flow connector to reduce its profile, and delivering the flow connector through the lumen of the delivery member into the first body space.

In some embodiments, the flow connector includes a flange radially extending from the conduit, and the step of delivering the implant to the first body space places the flange within the first body space. In some embodiments, when the flow connector is placed within the receiving area the flange of the flow connector extends beyond an outer wall of the delivery member.

The method of moving the deforming member to the second position can cause a folding block of the deforming member to press the conduit of the flow connector without contact with the flange to thereby fold the conduit into a U-shaped cross-sectional configuration.

In some embodiments, the first space within the body is a source element and the second space within the body is a destination element.

In some embodiments, the step of delivering the flow connector through the lumen of the delivery member comprises the steps of advancing a first plunger to move the flow connector from the receiving area to an intermediate position within the lumen of the delivery member and subsequently advancing a second plunger to deliver the flow connector out a distal opening of the delivery member.

In some embodiments, when the flow connector is delivered through the lumen, a toe portion of the flange is directed toward a distal end of the delivery member and a heel portion of the flange is positioned alongside the conduit extending proximally.

BRIEF DESCRIPTION OF THE DRAWINGS

Embodiments of the present invention are described herein in conjunction with the accompanying drawings, in which:

FIG. 1A is a side view of one embodiment of a flow connector of the present invention;

FIG. 1B is a top view of the flow connector of FIG. 1A taken along cross-section line 1B-1B in FIG. 1A;

FIG. 11 is a cross-sectional view similar to FIG. 10 showing the folding mechanism moved to the closed position to contact and fold the flow connector seated in the delivery sheath;

FIG. 12 is a cross-sectional view similar to FIG. 11 showing the folding mechanism in the closed position and the load plunger advanced to move the flow connector out of the receiving area and to an intermediate position further into the delivery sheath;

FIGS. 16A-16E illustrate the method of delivering the flow connector once it is positioned within the delivery sheath wherein FIG. 16A illustrates the delivery system approaching a first body space, e.g., a source element such as an artery; FIG. 16B illustrates the tip of the delivery sheath (cannula) inserted through an opening in the artery and into the lumen of the artery, with the sheath stop abutting the wall of the artery; FIG. 16C illustrates advancement of the deployment plunger to deploy the flow connector from the delivery sheath into the arterial lumen; FIG. 16D illustrates the flow connector positioned in the artery with the flange of the flow connector engaging the internal wall of the artery and a second body space, e.g., a destination element such as a vein, being advanced toward the flow connector, and FIG. 16E illustrates the vein placed over the conduit portion of the flow connector;

FIG. 22 is a close up view showing the deployment plunger shaft and load plunger bore;

FIG. 23 is a cross-sectional view taken along line 23-23 of FIG. 22; and

FIG. 24 is a view similar to FIG. 22 showing the deployment plunger shaft and load plunger bore from the other side.

DETAILED DESCRIPTION

Figure 1C:
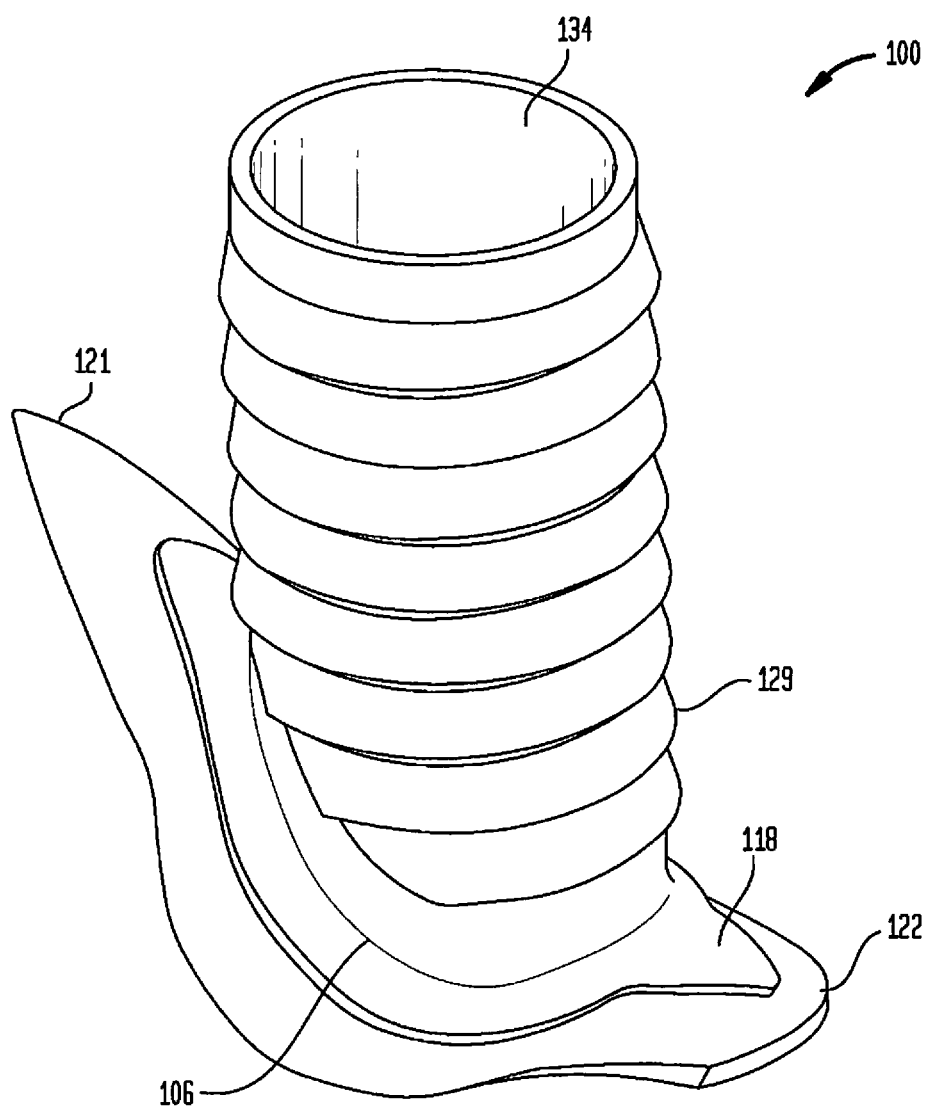
FIG. 1C is an isometric view of another embodiment of the flow connector of the present invention.

Aspects of the present invention are generally directed to a delivery system for delivering an implant to a body space. In accordance with a preferred embodiment, the delivery system is intended to deliver an implantable flow connector which is configured to be implanted in a tissue-enclosed body space such as a body conduit or body reservoir to provide a flow path for fluid from the source body space to another body space, a man-made or body conduit, an external or implanted medical device, or other destination element. Before discussing the delivery system, details of the implantable flow connector will first be described. However, it should be understood that the delivery system can also be used to deliver other implants to a body space.

In one embodiment of the flow connector, the connector has a conduit having a lumen that terminates at an orifice on opposing ends of the conduit, and a flange radially extending from one of the two ends of the conduit. The flow connector is configured to be implanted into the source body space via a natural or artificial opening (e.g., a man-made opening) in a region of the tissue wall that defines the body space. The flange surrounds the conduit orifice through which the conduit lumen is fluidically coupled to the interior of the body space, and is configured to be self-retained in the body space.

The conduit is also configured to be retained in the noted destination device or body space or body region (collectively and generally referred to herein as the destination element). For example, when the destination element is a tissue-enclosed body space, the conduit is configured to be implanted into the destination body space via a natural or artificial opening in the tissue wall defining that body space. Once implanted, fluid exiting the conduit orifice at the distal end of the flow connector flows into the destination element. As such, the flow connector of the present invention fluidically couples the source body space and destination device or body space.

As noted, embodiments of the flow connector of the present invention may be used to fluidically couple any tissue-enclosed body space to any type of destination including any other tissue-enclosed body space, other areas in the body, or an external or implanted medical device. Embodiments of the flow connector may be configured to be implanted in any tissue-enclosed body space including, but not limited to, body conduits such as blood vessels, lymph ducts, tear ducts, bowels, urethra, etc., which have a lumen through which fluid is carried to facilitate circulation, excretion or other fluid transfer, as well as body reservoirs such as the stomach, bladder, gall bladder, lymph nodes, etc., which temporarily or permanently retain fluid. For ease of description, embodiments of the flow connector described below are specifically configured for implantation to create an arteriovenous (AV) fistula and, more specifically, an AV fistula in the upper or lower extremity to provide vascular access for hemodialysis patients.

FIG. 1A is a side view of one embodiment of a flow connector of the present invention. In FIG. 1A, flange 102 is a circumferential flange and is configured to radially extend from conduit 104 proximate to its first or proximal end 131 of conduit 104. Conduit 104 terminates at proximal end 131 of conduit 104 at an orifice. A second orifice is disposed on the opposite side of conduit 104 at its distal end 132. Flange 102 comprises a contact surface 126, which is configured to contact an inner surface of the tissue wall defining the source body space of a recipient when it is implanted therein. On the opposite side of flange 102 from contact surface 126 is an exposed surface 128 which is exposed to fluids passing through the source body space (not shown).

Figure 1D:
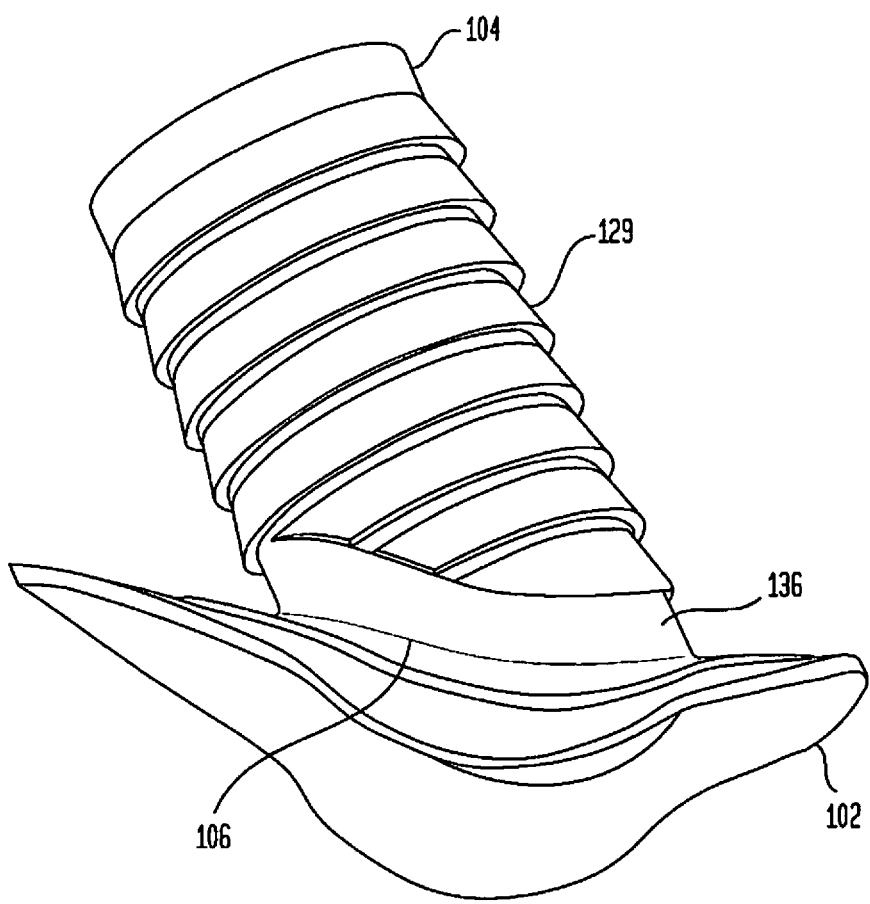
FIG. 1D is another isometric view of the embodiment of the flow connector illustrated in FIG. 1C.

In one embodiment of the present invention, flange 102 comprises a plurality of circumferentially adjacent sections. For example, a pair of opposing flange sections 112A and 112B could be provided. In those embodiments designed for implantation in a body conduit, flange sections 112 are referred to as longitudinal flanges, and flange section 112A is referred to as heel section 112A while flange section 112B is referred to as toe section 112B. In addition to longitudinal sections 112, there is a pair of substantially similar lateral sections 114A, 114B extending from opposing sides of conduit 104 approximately equidistant from flanges 112A, 112B. Circumferentially opposed sections 114A, 114B, also referred to herein as lateral sections 114 due to their substantially orthogonal positioning relative to longitudinal sections 112, are configured to extend from flange 102 as illustrated in FIGS. 1C-1E, on opposing sides of conduit 104, and are further configured to extend circumferentially around a longitudinal axis 110 of the source body space in which flange 102 is to be implanted. The circumferential radius of lateral sections 114A, 114B is selected based on the radius of curvature of the region of the source body space in which flow connector 100 is to be implanted. In one embodiment, the radius 297 defined from longitudinal axis 110 to contact surface 126 of lateral sections 114A, 114B is substantially equal to the radius 298 defined from longitudinal axis 110 to the inner surface of the source body space. In other embodiments, radius 297 defined from longitudinal axis 110 to contact surface 126 of lateral sections 114A, 114B is larger than the radius 298 defined from longitudinal axis 110 to the inner surface of the source body space. The larger radius of lateral sections 114A, B combined with the nature of the memory material with which it is constructed will generate a chronic outward force when flow connector 100 is implanted within the source body space, which will in turn cause the walls of the source body space to resist the outward force, thereby providing a compression force to lateral sections 114A, B. The compression force applied to lateral sections 114A, B in turn urges contact surface 126 of flange 102 towards the opening in the tissue wall of the source body space, thus providing a seal between contact surface 126 of flange 102 and the tissue wall such that fluid within the source body space will not leak after implantation of flow connector 100. It is to be understood that in one embodiment of the present invention, some fluid from the source body space may or may not leak immediately after implantation. However, with normal physiological healing processes, such leakage will soon thereafter cease as the aforementioned seal will be provided by contact surface 126 on flange 102 with the tissue wall, thereby eliminating the need for additional elements such as glue, sutures etc. in order to stop or prevent fluid leakage.

In addition to providing a seal between contact surface 126 and flange 102, as described above, the larger radius of lateral sections 114A, 114B combined with the nature of the memory material with which it is constructed also acts to provide support for flow connector 100. As used herein, supporting flow connector 100 refers to physically supporting flow connector 100 such that it retains its position within the source body space, after implantation, without other components or objects contributing towards the retaining of its implanted position.

In one embodiment of the present invention, lateral sections 114A, 114B extend circumferentially around the interior surface of the source body space so as to leave approximately 180° of the source conduit's interior surface circumferentially uncovered by lateral sections 114A, 114B and flow connector 100 generally. By leaving approximately 180° uncovered, obstruction to the flow of fluid within the source body space is minimized while enhancing stability provided by lateral sections 114A, 114B to flow connector 100 when implanted. Longitudinal sections 112 are also circumferentially curved with respect to the interior surface of the source body space such that contact surface 126 makes contact with the interior surface of the source body space in a sealing region 116, thereby providing a hydrophobic seal as well as stability between flow connector 100 and the source body space.

Adjacent to sealing region 116 is reinforcement region 118, configured to provide physical support to flow connector 100 by being constructed and arranged to oppose various explanting or other forces that may be exerted on flange 102 and conduit 104 when flow connector 100 is implanted in the source body conduit. Reinforcement region 118 is configured to have a rigidity that it aids in the opposition of deflection forces, and is therefore less prone to flexing of portions of flange 102 and/or conduit 104. The rigidity of reinforcement region 118 decreases in a radially-increasing direction thereby aiding in the implantation of flange 102 in the source body space. It should be appreciated that the rigidity may be provided in various ways, according to various embodiments of the present invention. By avoiding substantial deflecting or bending, flange 102 remains larger than the aperture in the source body space through which flange 102 was inserted, thus preventing explanting or pull-out from the source body space. As used herein, substantial deflecting by flange 102 refers to the reduction of the surface area of flange 102 to a size allowing flange 102 in its deflected state to fit through aperture in the source body space through which flange 102 was inserted.

Reinforcement region 118 is proximal to conduit 104 so as to provide structural integrity to conduit 104 such at the orifice at the proximal end 131 of conduit 104 can withstand a greater amount of compression force than without reinforcement region 118 being present. As will be further discussed below, reinforcement region 118 also may assist in opposing explant forces that may be applied, intentionally or inadvertently, on flow connector 100.

Longitudinal sections 112 are configured to facilitate implantation of flow connector 100 while also opposing pull-out forces which may otherwise pull flow connector 100 out from the source body space (not shown) after flow connector 100 is implanted. Lateral sections 114A, B are also configured to facilitate implantation and further configured to maintain the position of flow connector 100 with respect to the source body space (not shown) after flow connector 100 is implanted. In one embodiment of the present invention, lateral sections 114A, B have a radius of curvature substantially identical to the radius of curvature of the source body space into which it is to be implanted. In other embodiments of the present invention, lateral sections 114A, B has a curvature radius which is slightly larger than the curvature radius of the source body space into which it is to be implanted. When this embodiment is implanted in the source body space, the larger curvature radius of lateral sections 114A, B will cause the source body space to generate compression forces on the larger lateral sections 114A, B which will in turn promote the maintenance of the position of flow connector 100 in the source body space.

FIG. 1B is a cross-sectional view along the line 1B-1B noted in FIG. 1A, in which a substantial portion of the conduit body 130 is shown as if removed for the purpose of showing an unobstructed view of the longitudinal sections 112 and lateral sections 114. In the embodiment shown in FIG. 1B, heel section 112A and toe section 112B have apices, heel section apex 121 and toe section apex 122, respectively, when viewed from the perspective illustrated in FIG. 1B. In this embodiment, heel section apex 121 and toe section apex 122 come to a sharp point which may be helpful in redirecting fluid flowing within the source body space so as to prevent or minimize disturbances in flow shear stress, eddy flow, foil effects, turbulence, resistance, tube wall deformation, and tensile stress/strain distributions that can lead to intimal hyperplasia and other similar or associated conditions. Similarly, as depicted in FIG. 1A, flange edge 140 may be chamfered to an angle, for example 60°, so as to similarly redirect fluid flowing within the source body space for the same purpose.

Multiple cutout regions 124 are disposed between longitudinal sections 112 and lateral sections 114. Cutout regions 124 represent an absence of material between those flanges 112, 114 and are dimensioned and configured to facilitate temporary foldover of flanges 112, 114 during implantation of flow connector 100. Sealing region 116 is also disposed over a portion of cutout regions 124 to ensure that the contact surface 126 around conduit body 130 is sealed with respect to the source body space so that fluids flowing through the source body space remains either within the source body space or through the lumen of conduit 104.

As noted above, flow connector 100 also comprises conduit 104 which is connected to flange 102 along joint region 106. At joint region 106, the proximal end 131 of conduit body 130 and flange 102 are joined such that first conduit orifice 120 leads into the lumen of conduit body 130. In the embodiment illustrated in FIGS. 1A and 1B, conduit portion 106 is depicted largely as comprising a cylindrical conduit body 130. However, it is to be appreciated by one having ordinary skill in the art that conduit body 130 may have other shaped tubular bodies other than a cylindrical one in other embodiments of the present invention. For example, in other embodiments of the present invention, conduit body 130 may comprise a conduit body 130 with a rectangular or irregular cross section and a similarly shaped longitudinal lumen disposed therein. On the opposite end of conduit body 130 from proximal end 131 is distal end 132 of conduit body 130 as well as second conduit orifice 134 which is disposed at distal end 132. Second conduit orifice 134 allows fluid flow traveling through the lumen of conduit body 130 to exit through second conduit orifice 134. For example, in one embodiment of the present invention in which a source body space, such as a vein or artery, is coupled to conduit 104, fluid flowing through the source body space into which flange 102 is implanted is diverted through first conduit orifice 120, through the lumen of conduit body 130 and out of second conduit orifice 134 into the source body space.

Although the construction of flow connector 100 may vary depending on the one or more source conduits in which flow connector 100 is to be implanted, embodiments of the present invention may differ in terms of the material comprising flow connector 100, the durometer values of materials selected, thicknesses of the various components of flow connector 100 described herein or shown in the figures, and are considered a part of certain embodiments of the present invention. In one embodiment, flange 102 has a thickness ranging between approximately 0.15 mm and approximately 0.35 mm. Similarly, the outside diameter of conduit body 130 has a similar thickness range between approximately 0.15 mm and 0.50 mm and more preferably, of between approximately 0.30 mm and approximately 0.45 mm. In another embodiment, the outside diameter of conduit body 130 has a thickness of approximately 0.35 mm. The thickness of flange 102 may be decreased as flange 102 is made to extend further which will maintain the pullout forces necessary for flange 100 to be pulled out of the source body space in which it is implanted. Similarly, the thickness of flange 102 may be increased as the flange 102 is made to extend less.

As shown in FIG. 1C, conduit body 130 may comprise a series of barbs or protrusions 129 which extend radially from conduit body 130. In one embodiment of the present invention, the protrusions 129 provide periodic increases in the outside diameter of conduit body 130 so that the source body space within which conduit body 130 is inserted are positioned over conduit body 130 in a friction fit over the increased diameter portions of protrusions 131. Furthermore, once the source body space is positioned over conduit 104 over protrusions 131, one or more sutures may be disposed circumferentially around conduit body 130 and in the areas between conduit body 130 and the outer diameter of protrusions 131, thereby snugly retaining the source body space in place with respect to conduit 104. When one or more sutures are thus disposed, the one or more sutures that compress the source body space towards the conduit portion 104 will maintain its position since the diameter of the one or more sutures are fixed to be smaller than the outer diameter of the protrusions, which therefore provides an interference fit to prevent the one or more sutures from translating along the longitudinal axis 108 of conduit body 130.

Figure 2A:
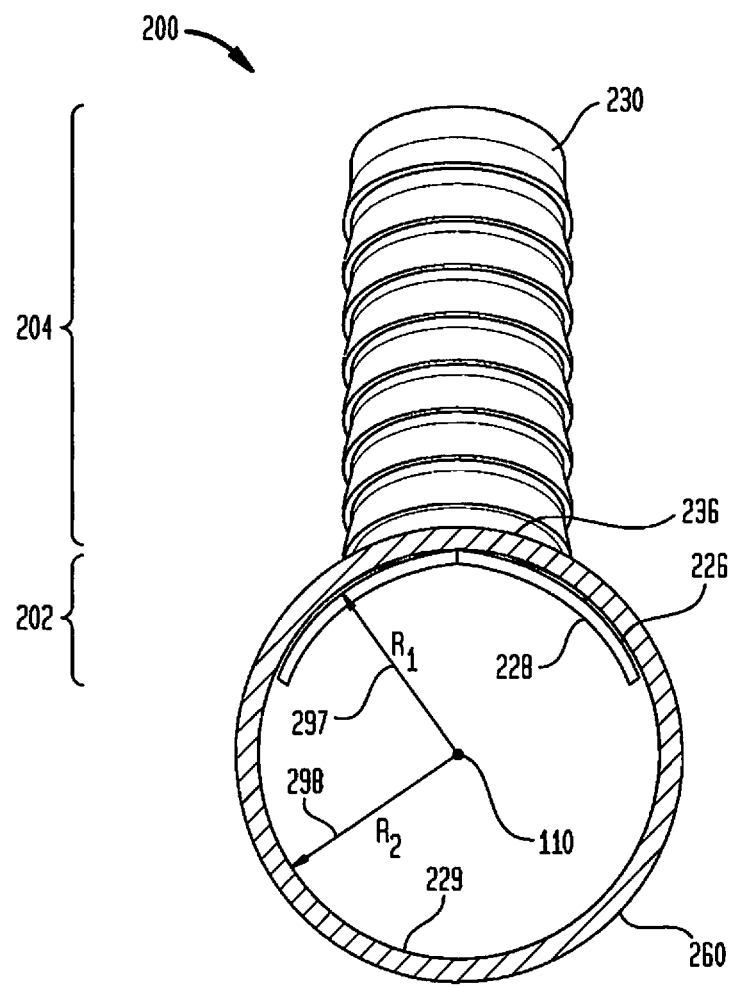
FIG. 2A is a cross-sectional view of a first tissue-enclosed body space in a patient having one embodiment of the flow connector of the present invention implanted therein.
Figure 2B:
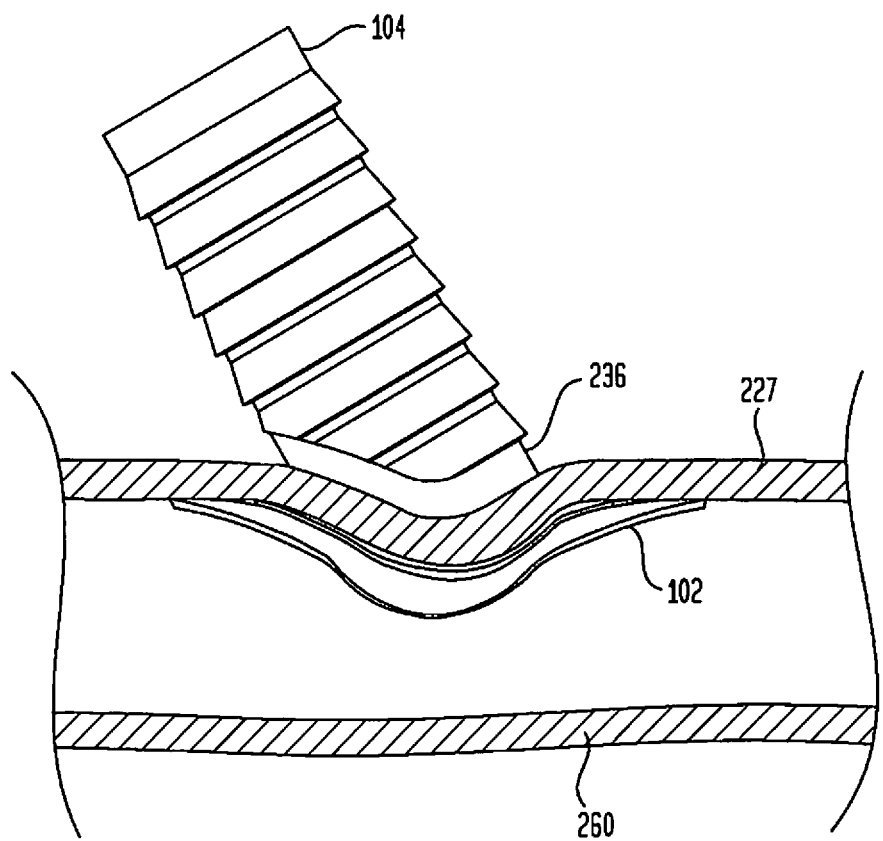
FIG. 2B is another cross-sectional view of a first tissue-enclosed body space in a patient having the flow connector of FIG. 2A implanted therein.

In certain embodiments of the present invention, conduit body 130, shown in FIGS. 2A and 2B as conduit body 230, has a conduit recess 236 disposed thereon. Conduit recess 236 is configured such that a source body space, such as source body space 260, rests within conduit recess 236 when flange 102, shown in FIGS. 2A and 2B as flange 202, is positioned within the source body space as described below. Conduit 204 of one embodiment of the present invention is shown to be angled approximately 60° from the horizontal axis in the illustration with respect to flange 202. This angle may vary in other embodiments of the present invention depending on the situation or the needs of the recipient. For example, in other embodiments of the present invention, conduit 204 may be configured with an angle between 10° to 90° from the horizontal axis shown in FIG. 2B. As one having skill in the art would appreciate, this angle can be from the opposite side as well with respect to flange 202.

As noted previously, flow connector 100, shown in FIG. 3 as flow connector 300, is configured to be at least partially placed within a source body space. In the embodiment illustrated in FIG. 3, flange 102 is configured to be positioned through an opening 303 on source body space 360. More specifically, one or more of heel section 312A, toe section 312B, and lateral sections 314A, B are temporarily deformed or bent with respect to flow connector 100 so that flange 102 can be inserted through opening 303. Opening 303 may be an existing opening or may be manually and/or intentionally formed, at least in part, to allow flange 102 to be inserted therethrough during the implantation of flow connector 300 within source body space 360. In the embodiment shown in FIG. 3, heel section 312A is longer than toe section 312B. The greater length of heel section 312A is configured to promote stability and the position of flange 102 within source body space 360. Additionally, the shorter length of toe section 312B, in the present embodiment of the invention, is configured to promote easier insertion of flange 102, especially in implantation methods where only lateral sections 314A, B are temporarily deformed, with longitudinal sections 312 inserted through opening 303 in their substantially extended position.

Figure 3:
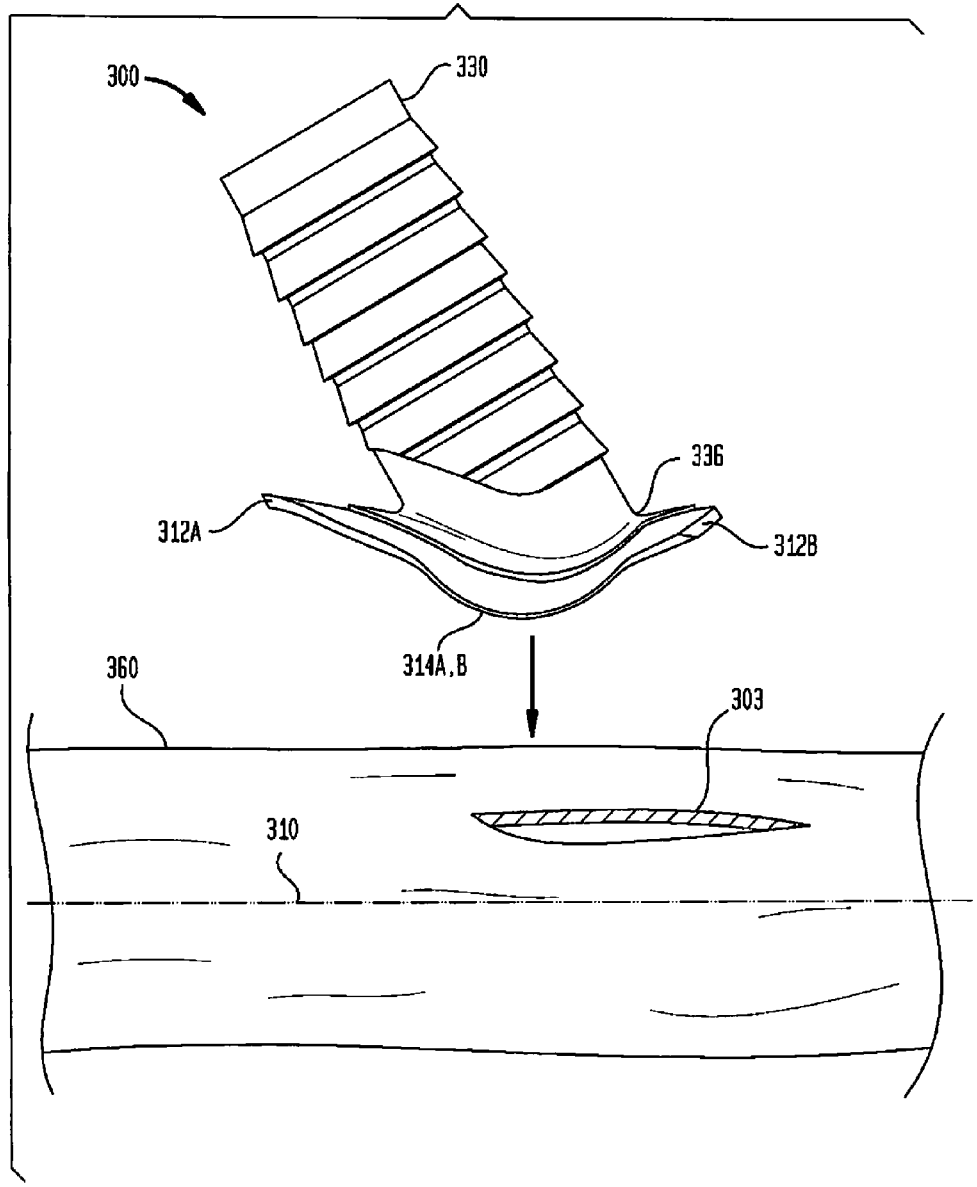
FIG. 3 is a perspective view of another embodiment of the flow connector of the present invention illustrated with respect to a tissue-enclosed body space into which the flow connector of the present invention is to be implanted.

In the embodiment illustrated in FIG. 3, the fluid flowing substantially along longitudinal axis 310 through source body space 360 is flowing from the direction of heel section 312A and flowing towards the direction of toe section 312B. As is seen in the embodiment illustrated in FIGS. 1 and 3, the longitudinal axis 108 of conduit body 130 is angled with respect to the longitudinal axis 310 of source body space 360 at an angle of approximately 60° towards to direction of heel section 312A. In this embodiment of the present invention, the 60° angled source body space 360 is provided to promote, among other things, a controlled rate and/or volume of fluid flow from source body space 360 into conduit body 330. In other embodiments of the present invention, that angle may not be 60°, but may instead be some other angle, depending on the placement of flow connector 300 within the recipient or the purpose for which flow connector 300 will be used once implanted. For example, in other embodiments of the present invention, conduit body 330 may be angled 90 or 120° with respect to longitudinal axis 310 in order to achieve a desired rate or volume of flow from source body space 360.

Figure 4:
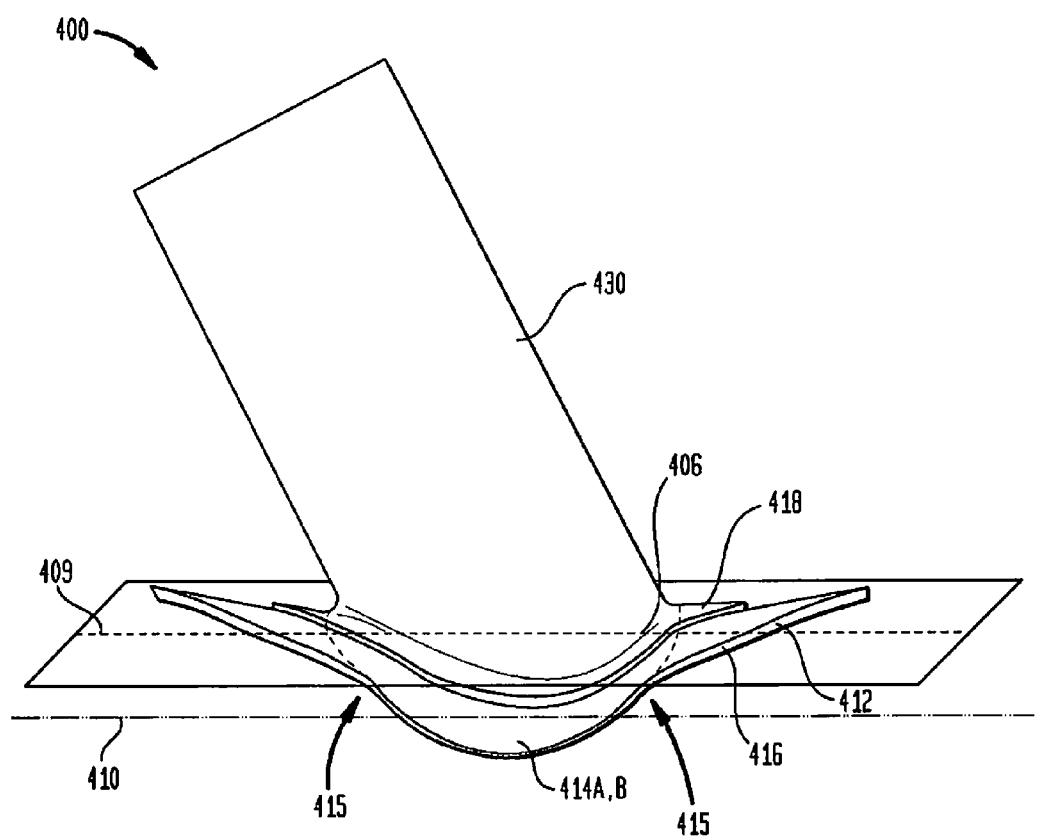
FIG. 4 is a perspective view of one embodiment of the flow connector of the present invention with an imaginary plane having an imaginary midline.
Figure 5:
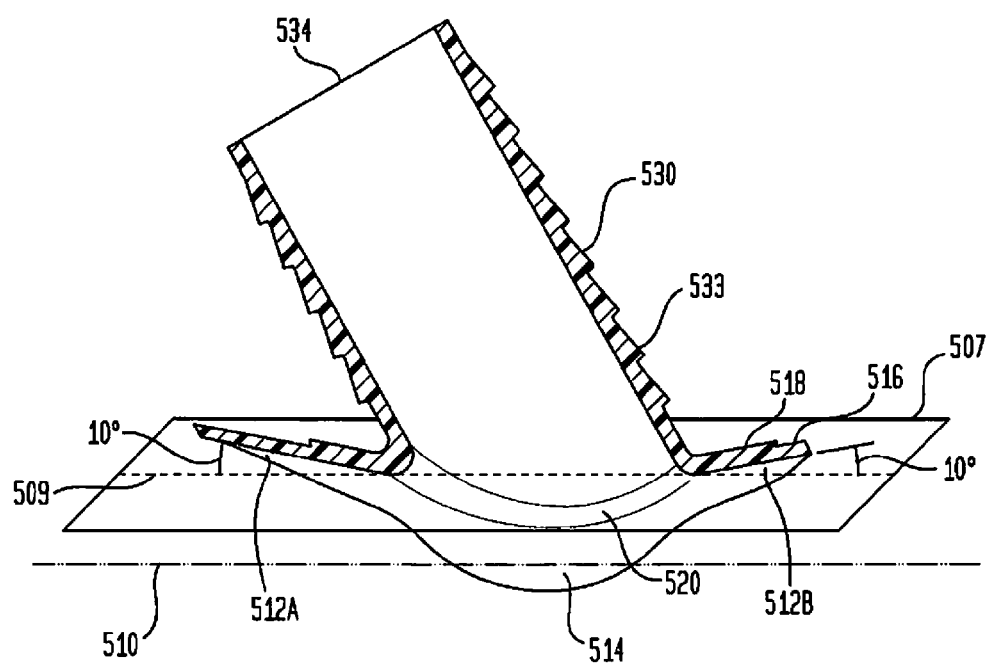
FIG. 5 is a cross-sectional view of one embodiment of the flow connector of the present invention with an imaginary plane having an imaginary midline.

In FIGS. 4 and 5, an imaginary plane having a midline 409 is shown with respect to flow connector 400 and longitudinal axis 410 of source body space (not shown), according to one embodiment of the present invention. Midline 409 is parallel with respect to longitudinal axis 410 and is disposed on the exposed surface 128 around first conduit orifice 120. In the embodiment depicted, longitudinal sections 412 are angled upwards 10° from midline 409 starting at transition points 415 as shown. In other embodiments of the present invention, longitudinal sections 412 may be angled by a different amount, for example between 0 and 15°. The angling of longitudinal sections 412 upwards towards the inner surface of the source body space in which flow connector 400 is implanted will cause to be generated one or more deflection forces as a result of longitudinal sections 412 being pressed into the wall of the source body space. These deflection forces will cause a deflection of longitudinal sections 412 downward such that longitudinal sections 412 will be more parallel with midline 409 and longitudinal axis 410 of the source body space. This deflection downward will permit later flanges 414A, B to be disposed closer to the inner wall of the source body space than if the deflection did not occur, and will also cause a broader contact between contact surface 126 and the inside wall of the source body space once flow connector 400 is positioned within the source body space. FIG. 5 illustrates the imaginary lane with midline 409, now shown as midline 509, as well as the 10° angling of longitudinal sections 412, now shown as longitudinal sections 512, with respect to longitudinal axis 510 of the source body space.

Various alternate embodiments of the flow connector are disclosed in U.S. Pat. No. 8,366,651 and U.S. patent publication 2009/0036820, the entire contents of which are incorporated herein in their entirety by reference. The delivery system of the present invention can be utilized to deliver these alternate flow connectors as well.

Additionally, the delivery system can also be utilized to deliver the flow connector through the retention devices of U.S. application Ser. No. 13/792, 019, filed Mar. 9, 2013, and Ser. No. 13/792,012, filed Mar. 9, 2013,the entire contents of which are incorporated herein by reference. An example of a retention device through which the delivery system can be inserted is shown by way of example in FIG. 17 and discussed in more detail below.

Figure 6:
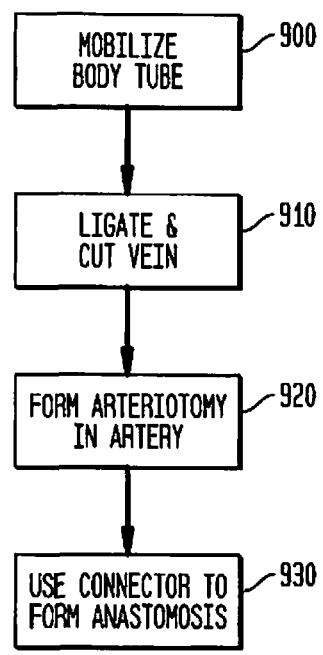
FIG. 6 is a high level flowchart of a method for implanting a flow connector according to one embodiment of the present invention.

In operation, embodiments of the present invention may be implanted in numerous ways. In one particular method of operation as depicted in the flow chart FIG. 6, the source body space is mobilized 900 from other conduits fluidically coupled to the destination body space. The destination body space, for example a vein of a recipient, is ligated and then cut 910 to receive the conduit 104 of flow connector 100. Once the destination body space has conduit 104 fitted therein, an opening is formed 920 in the source body space. Flange 102 of the flow connector, having the destination body space coupled thereto, is inserted through the formed opening in order to join 930 the source and destination body spaces together. In an alternate embodiment, the flow connector 100 is first inserted within the source body space and subsequently the destination body space is placed over the conduit 104 of the flow connector 100.

The outer diameter of the conduit preferably ranges from about 2 mm to about 8 mm, and preferably is about 4 mm. The inner diameter of the conduit preferably ranges from about 1.5 mm to about 7.5 mm, and preferably is about 3.5 mm. Other dimensions are also contemplated.

In certain embodiments of the present invention, the second end of conduit 104 is configured to have an inside diameter approximately equal to the inside diameter of the destination element's lumen, for example the lumen in a blood vessel. As discussed previously, matching the inside diameters of the distal end of conduit 104 and the destination element at the point in each where fluid flow transitions from one to the other significantly reduces eddy current flow and other disturbances in the flow, which in turn reduces the occurrence of clots, thrombus, intimal hyperplasia, and other conditions which are largely undesirable.

Embodiments of the present invention may be configured to aid in the retention of the destination element on the distal end of the conduit. In some embodiments, radial protrusions are disposed circumferentially around the exterior surface of the conduit, either along the entire length or a portion thereof. According to another embodiment of the present invention, protrusions may be disposed on a separate collar and positioned on the conduit prior to implantation of flow connector. Various protrusions and various arrangements of protrusions, to cooperate with suture or collars, are disclosed in U.S. patent publication 2009/0036820 and U.S. Pat. No. 8,366, 651.

In other embodiments of the present invention, the retention feature provided on the surface of the conduit may be surface treatments, such as dents or dimples, such that the treated exterior surface provides retention. Depending on the size of the dimpling or denting surface treatment, the exterior surface can be configured to provide a friction fit on the interior surface of the destination element, for example a blood vessel. Other retention features may be provided on the exterior of conduit such as barbs which can be configured such that they at least partially pierce the wall of the destination element, for example a blood vessel, in order to retainingly secure the element on the conduit. In other embodiments of the present invention, the barbs can pierce through the destination element while retainingly securing the destination element on the conduit.

Flow connector 100, 200 further comprises a rest surface 136, 236 on conduit 104 adjacent the joint region 106, as illustrated in FIGS. 1D and 2B according to yet further embodiments of the present invention. In the embodiment illustrated in FIG. 1D, rest surface 136 is a recess in the body of conduit 104 configured to receive a wall of the source body space around rest surface 136 once flange 102 is implanted therein. In the embodiment illustrated, rest surface 136 is substantially smooth and free of protrusions 129 described above which are configured to retain the destination element once the destination element is positioned over protrusions 129. In the embodiment illustrated in FIGS. 1D and 2B, rest surface 136 is shaped with a curve, and source body space 227 is shown in FIG. 2B as conforming to the curved shape of rest surface 136. However, the degree to which body space 227 is shown to curve in FIG. 2B is exaggerated for illustrative purposes and may not always take the degree of curvature depicted.

In addition to the protrusions described above being used to retain the destination element upon being fit on the protrusions, the protrusions may also be used to receive one or more retaining elements such as sutures or a securing collar. In one embodiment, two sutures are placed on the destination element, e.g., vein, in order to compress the vein towards recesses disposed along the exterior surface of the conduit. Adjacent protrusions can cooperatively form angled recess therebetween into which retaining elements such as sutures can compress the destination element at least partly into. The retaining elements can compress the destination element, such as the tissue wall of a vein, in between the spaces between protrusions. In an alternate embodiment, a securing collar may be used with a portion of the destination element, for example the tissue wall of a vein, disposed between the securing collar and conduit to secure the destination element on the conduit. In certain embodiments of the present invention, the destination element portion may be compressed by the securing collar against the exterior surface of the conduit. In other embodiments of the present invention, the securing collar may press the destination element portion into correspondingly shaped recesses along the exterior surface of the conduit such that an interference fit between the recesses and securing collar 1169 will retain the destination element portion on conduit 1104.

It is to be understood that embodiments of the present invention may be used to connect flow connector described herein with an artificial conduit. In this manner, flow connectors may be used in bypass or other procedures which can benefit from one or more flanges which provide fluidic coupling as well as self-sealing and self-supporting features, among others.

It is to be understood that although embodiments of the present invention have been largely described as being used to connect two tissue-enclosed body spaces, for example veins and arteries, other embodiments of the present invention may be used to connect a body space to an artificial device, such as a pump, an artificial conduit connected to the flow connector 100 conduit 102, sensors, plugs, among others.

Turning now to the delivery systems of the present invention for delivering the above described flow connectors, and for delivering other variations of the flow connectors referenced in the patent applications incorporated by reference herein, FIGS. 7-16C illustrate a first embodiment of the delivery system and FIGS. 18-23 illustrate a second embodiment of the delivery system. In the first embodiment, the delivery plunger is a separate component insertable into the main delivery sheath (cannula) after the flow connector is in the loaded position; in the second embodiment, the delivery plunger is attached to the delivery sheath and is not a separable component. In both embodiments, the flow connector is positioned in a receiving area of the delivery sheath, deformed to a folded delivery state within the delivery sheath, advanced by a first load plunger to a loaded intermediate position within the delivery sheath, and then advanced by a second delivery plunger through the delivery sheath and out the distal end. Both of these embodiments are described in detail below. Note as used herein with respect to the delivery systems, the term distal refers to the region of the device further from the user and the term proximal refers to the region closer to the user.

Figure 7:
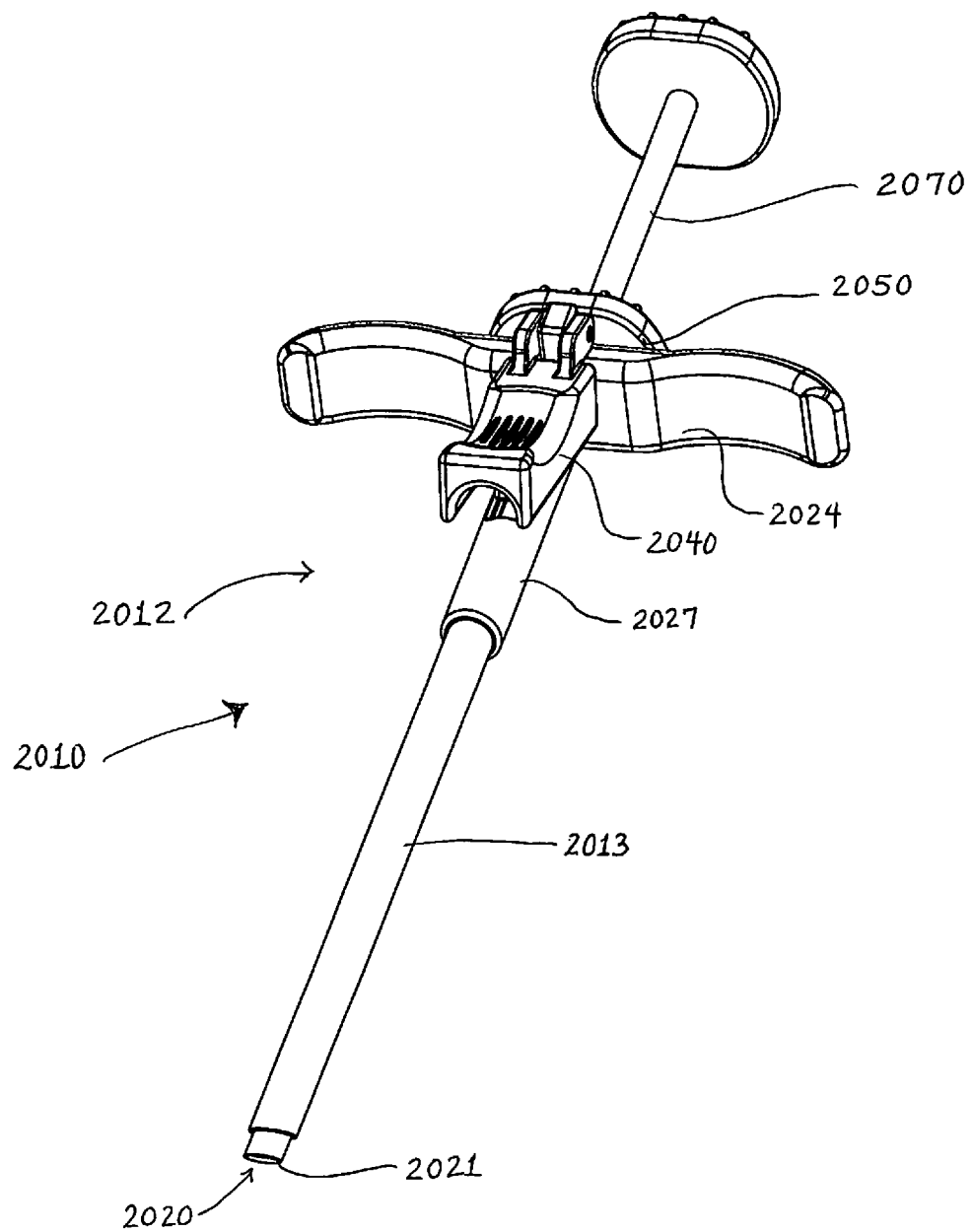
FIG. 7 is a perspective of a first embodiment of the flow connector delivery system of the present invention.
Figure 8:
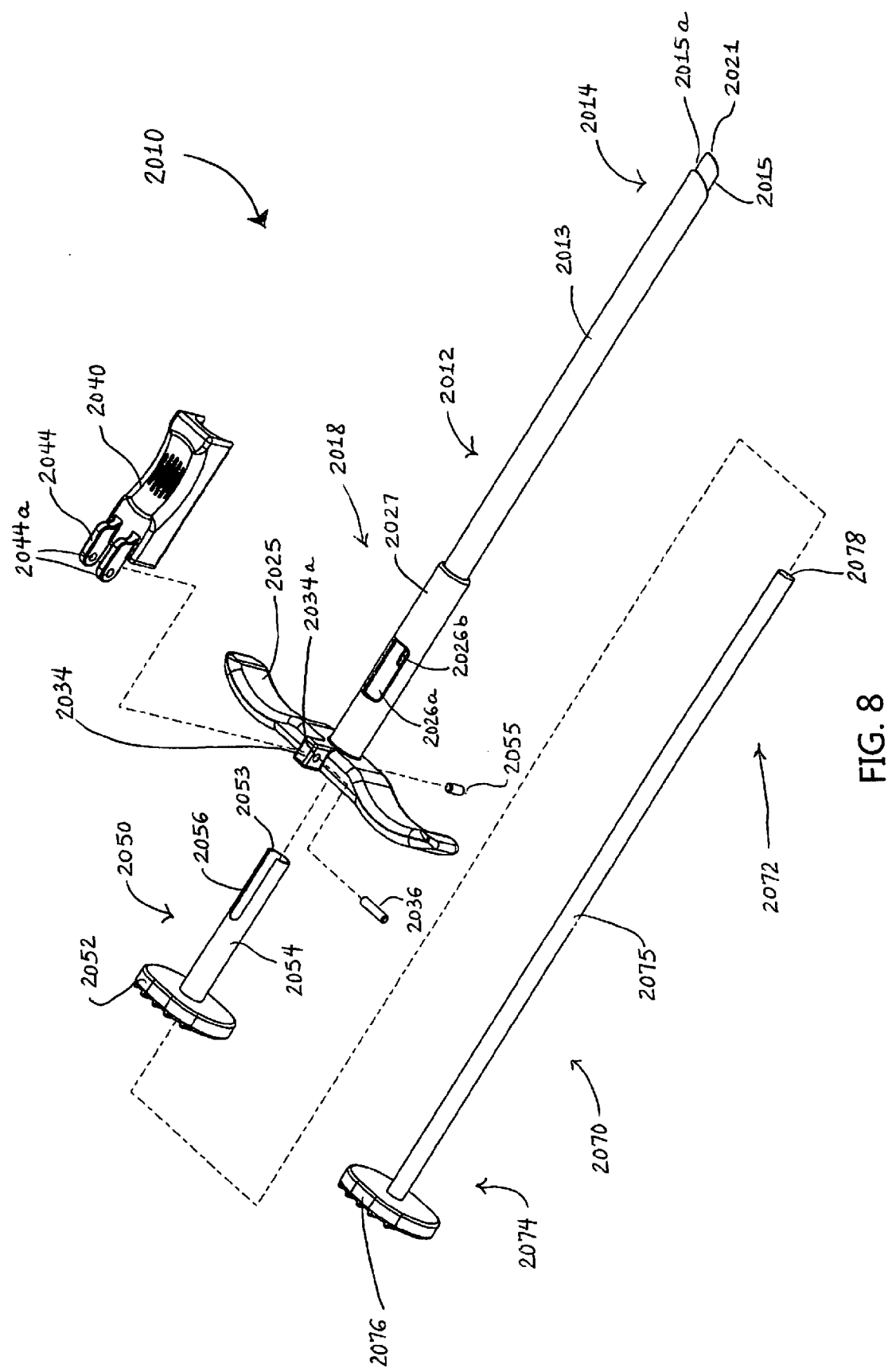
FIG. 8 is an exploded view of the delivery system of FIG. 7.

Turning first to the embodiment of FIGS. 7-16C, and with initial reference to FIGS. 7 and 8, the delivery system is designated generally by reference numeral 2010 and includes a delivery sheath or main cannula 2012, a deforming assembly 2040 and a first load plunger 2050. Second deployment plunger 2070 is a separate unit insertable through the load plunger 2050 and delivery sheath 2012.

Delivery member or sheath 2012 has a tubular member or delivery tube 2013 and a handle 2024. Delivery sheath 2012 further has a distal portion 2014, a proximal portion 2018, configured to remain outside the body, which includes the handle 2024 and a lumen 2017 (see e.g., FIG. 10) extending therethrough. In the illustrated embodiment, the delivery sheath 2012 is formed by attachment of the handle 2024 to the tubular member 2013, such as by injection molding or other methods with a distal region of the handle tube 2027 overlying a proximal portion of delivery tube 2013. However, it is also contemplated that the delivery sheath 2012 can be formed as a single unit.

The distal tip of the delivery sheath 2012 in preferred embodiments has a beveled end 2021 as shown. The distal region 2014 has a step portion 2015 of reduced outer diameter, preferably achieved by reducing the wall thickness so that the inner diameter, i.e., the diameter of the lumen 2017, does not change. This reduced diameter forms an edge 2015a which provides a stop to limit insertion of the delivery sheath 2012 and/or to provide a tactile feel to the user that the tip is in the desired position within the first body space as the edge 2015a abuts the outer wall of the body space. The lumen 2017 terminates at a distal end in distal opening 2020 for exit of the flow connector from the delivery sheath 2012 into the body space.

Figure 9:
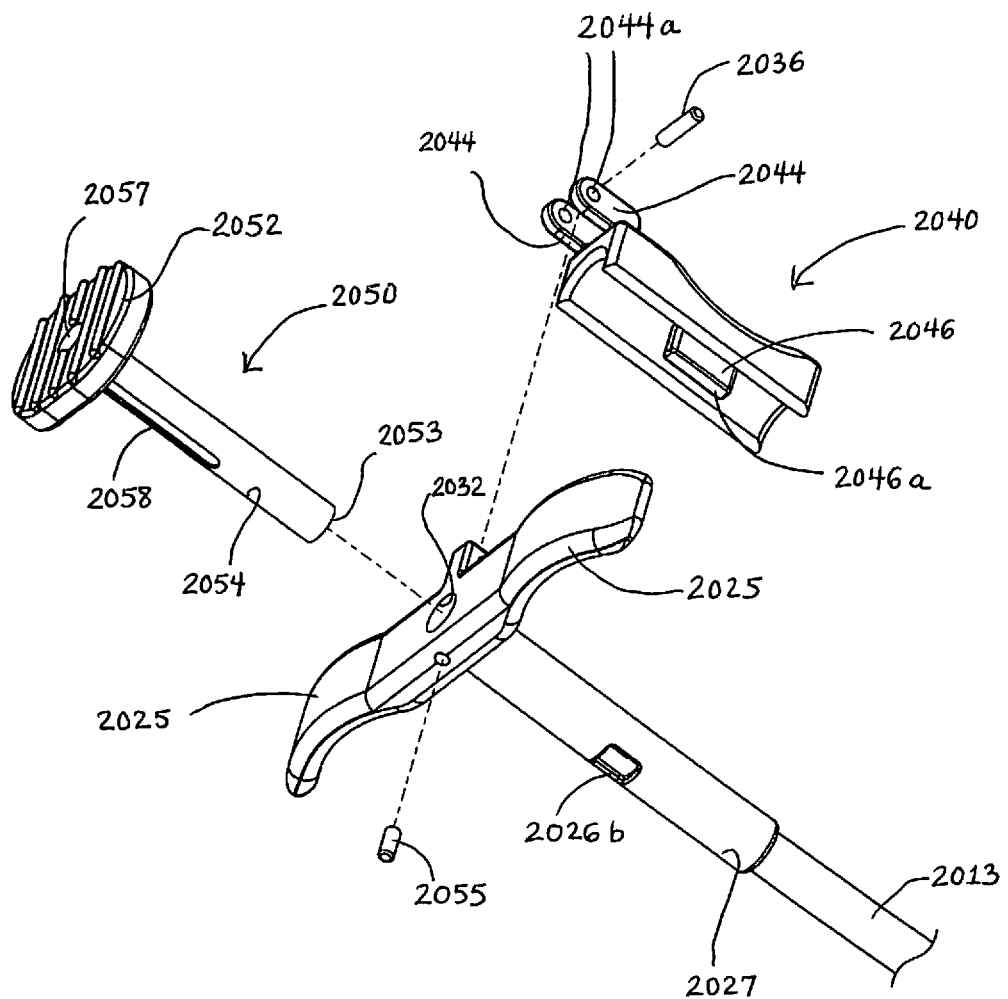
FIG. 9 is an exploded view illustrating the load plunger, folding mechanism and a proximal portion of the delivery member (sheath)
Figure 10:
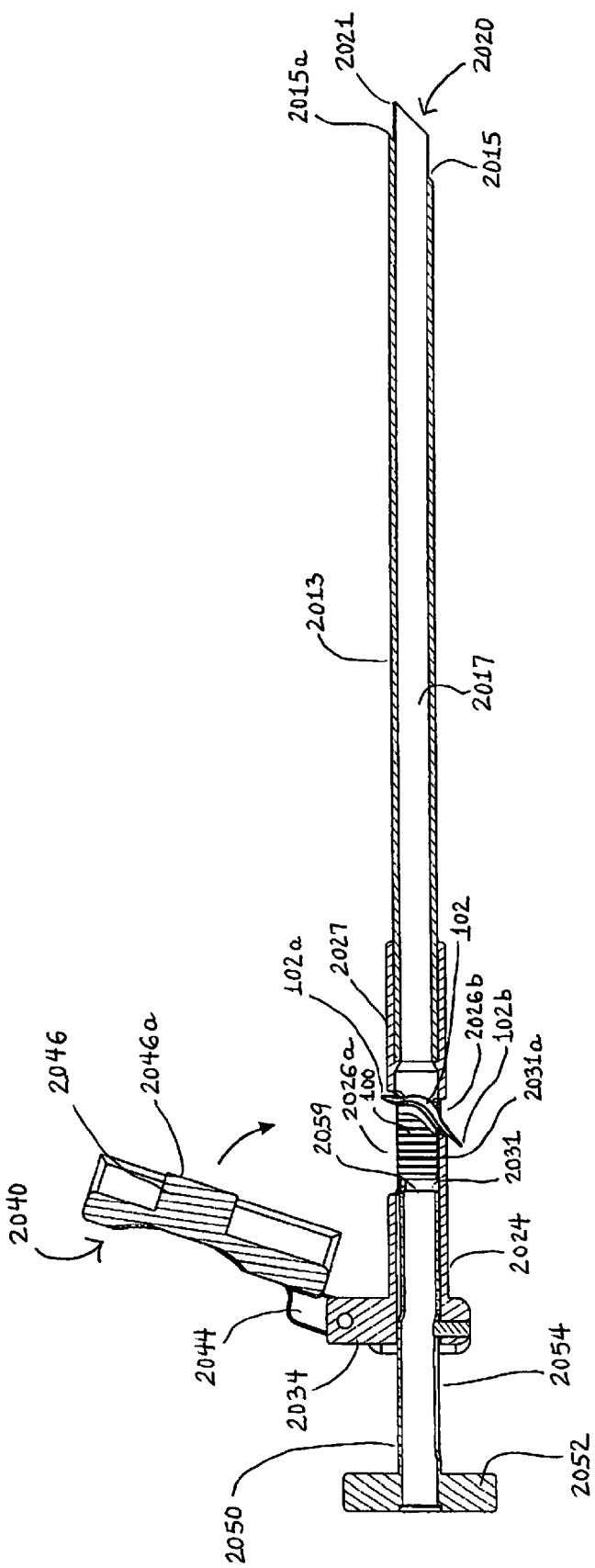
FIG. 10 is a cross-sectional view of the delivery system of FIG. 7 showing the folding mechanism in the open position to enable loading of a flow connector into the delivery sheath.
Figure 13:
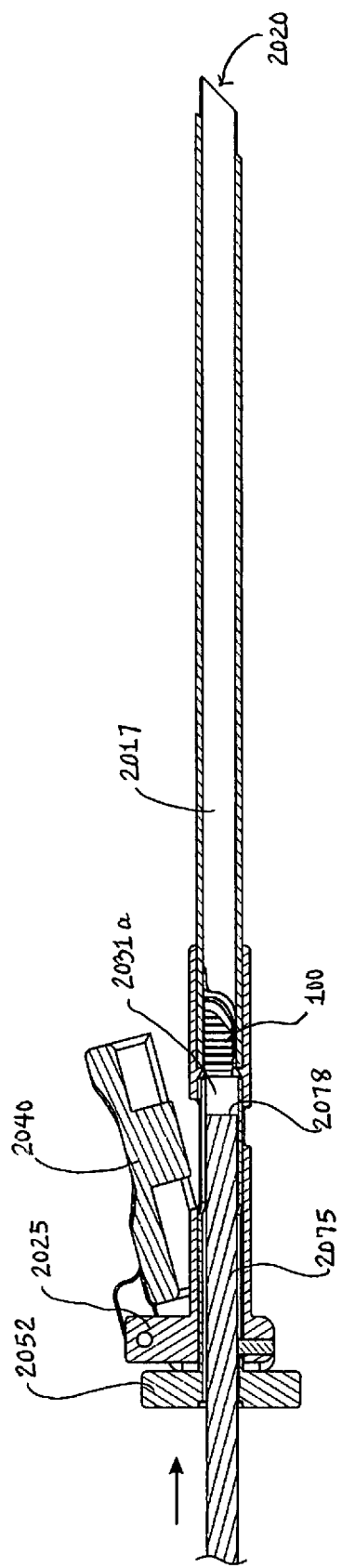
FIG. 13 is a cross-sectional view similar to FIG. 12 showing the folding mechanism moved toward the open position to enable advancement of the deployment plunger to move the flow connector out of the delivery sheath.

With reference to FIGS. 8-10, handle 2024 at the proximal end 2018 of the delivery sheath 2012 includes a handle tube 2027 and laterally extending handle grips 2025 with finger indentations to enhance gripping by the user. The handle tube 2027 includes a lumen 2031 which is longitudinally aligned with lumen 2017 of delivery tube 2013 and communicates with lumen 2017. Handle tube 2027 is positioned proximal of delivery tube 2013, and includes two opposed axially extending slots 2026a, 2026b formed in the wall of the handle tube 2027. Slot 2026a provides an opening to lumen 2031 of handle tube 2027 for insertion of the flow connector. Slot 2026b also communicates with lumen 2031 and provides an opening for the flange of the flow connector to protrude therethrough, described in detail below. Slot 2026a also allows another end of the flange to protrude beyond handle tube 2027. Slot 2026b can be a shorter length than slot 2026a since it only needs to receive a portion, e.g. the flange, of the flow connector. Thus, the two slots 2026a, 2026b form an opening on both sides of the tube 2027. A bore 2032 at the proximalmost end of the handle 2024 provides an entry for insertion of the load plunger 2050 and the delivery plunger 2070 into the lumen 2031 as described below.

With continuing reference to FIGS. 8-10, the deforming assembly is in the form of a folding assembly. Folding assembly or mechanism 2040 includes a folding block 2046, and mounting ears 2044 for receiving mounting pin 2036 for attachment to mount 2034 of handle 2024. The folding block 2046 is illustratively substantially rectangular shaped, however other shapes are also contemplated. Folding block 2046 is configured to contact and fold the flow connector as surface 2046a contacts the conduit portion of the flow connector (see also FIG. 11) as described below. Folding assembly or lever 2040 is pivotally connected to the handle portion 2024 of delivery sheath 2012 via pin 2036 extending through an opening 2034a in mount 2034 and openings 2044a in mounting ears 2044, although other methods of attachment are also contemplated.

Figure 14:
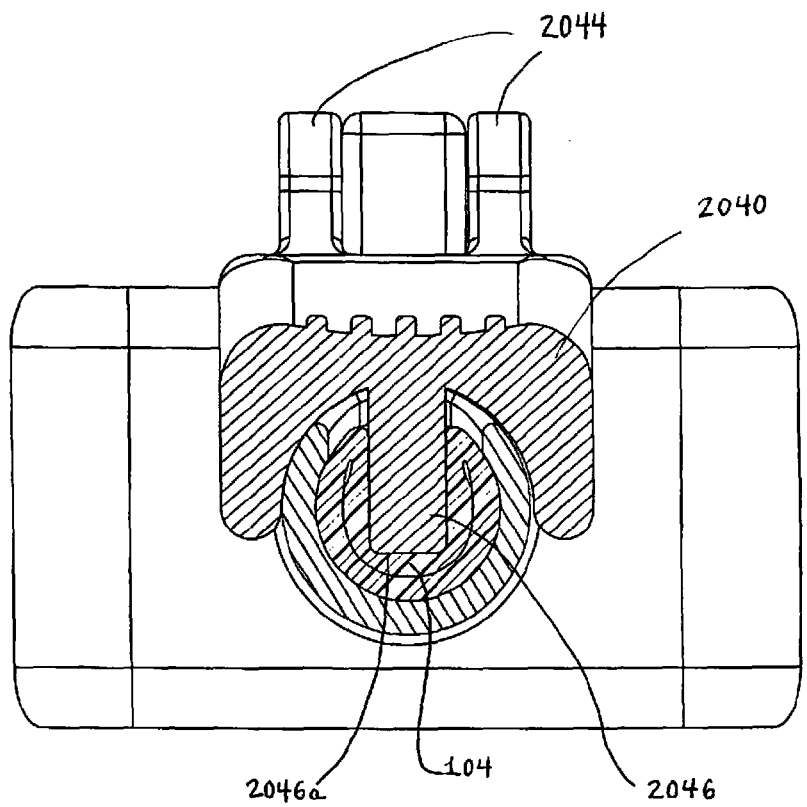
FIG. 14 is a cross-sectional view taken along lines 14-14 of FIG. 11.
Figure 15:
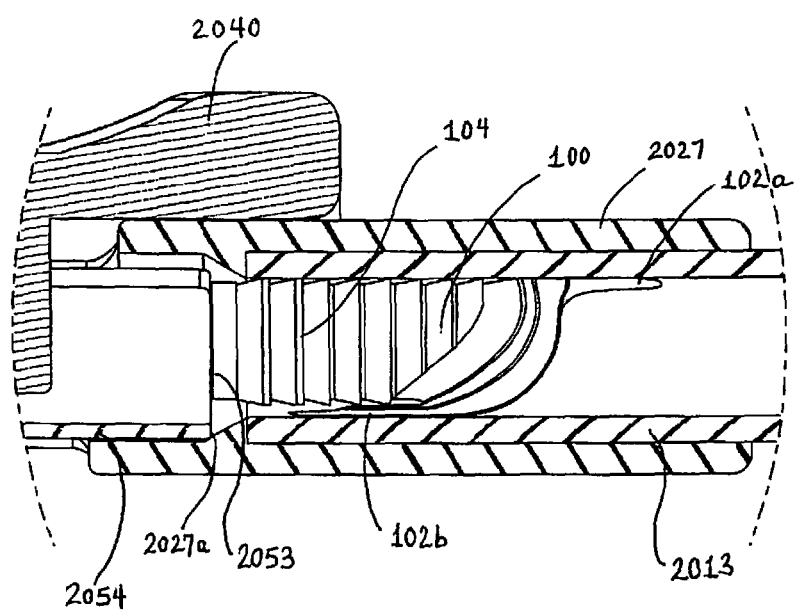
FIG. 15 is an enlarged view of the area of detail of FIG. 12.

Folding assembly 2040 is movable by the user from an open position to a closed position. In the open position of FIG. 10, the slot 2026a of the handle tube 2027 is exposed so that the flow connector, e.g. flow connector 100, can be inserted through slot 2026a into the receiving area 2031a of the lumen 2031 of the handle tube 2027 of the delivery sheath 2012. The receiving area 2031 a is shown as being in the handle tube portion of the delivery sheath, however, if the delivery tube is formed as an integral unit with handle, the receiving area would be in the lumen of the delivery tube. After placement of the flow connector in the lumen 2031, the folding assembly 2040 can then be pivoted by the user to a closed position (see FIG. 11) where the folding pin 2046 presses and applies a force to the conduit portion 104 of the flow connector 100 (see FIG. 14) to move it to the folded position for subsequent advancement through the lumen 2017 of the delivery tube 2013 of the delivery sheath 2012. As shown in FIG. 14, in this position, the flow connector has a U-shaped configuration in cross-section.

The load plunger 2050 is configured to advance the flow connector 100 from the load position in the receiving area 2031 a area of the delivery sheath 2012 to a predeployed (intermediate) or loaded position distal of the receiving area 2031 a in the lumen 2017 of the delivery tube 2013 of the delivery sheath 2012. Load plunger 2050, as shown in FIGS. 8 and 9, includes a handle 2052, illustratively disc shaped, although other configurations are also contemplated, a shaft 2054 and an elongated axially extending distal slot 2056. An elongated axial slot 2058 is formed in the opposing wall of the shaft 2054 at a proximal portion of the load plunger 2050. Axial slot 2056 is configured so that the load plunger can pass by the closed folding block 2046 when advanced (see FIGS. 11 and 12). Proximal axial slot 2058 is slid over pin 2055 as the load plunger 2050 is slid forward. Pin 2055 prevents the load plunger 2050 from disconnecting from the delivery sheath 2012 enabling slidable movement therein.

Load plunger shaft 2054 further includes a lumen 2059 (FIG. 11) extending therethrough and the handle 2052 has a bore 2057 at the proximal end communicating with the lumen 2059. Lumen 2059 communicates with lumen 2031 of handle tube 2027 and lumen 2017 of delivery tube 2013. Bore 2057 provides an entry for the deployment plunger 2070 so the plunger 2070 can advance through the lumen 2059 of the load plunger 2050 and into the lumens 2031 and 2017 of the delivery sheath 2012. The distal edge 2053 of shaft 2054 is configured to contact a proximalmost edge of the conduit portion 104 of the flow connector 100 to advance it from the receiving area 2031 a (see FIG. 11), past the axial slots 2026a, 2026b into the lumen 2017 of the delivery tube 2013 (see FIG. 12) as the load plunger 2050 is advanced. Internal wall 2027a of handle tube 2027 (FIG. 15) limits distal advancement of load plunger 2050.

Deployment plunger 2070 has a distal end portion 2072 and proximal end portion 2074 as shown in FIG. 8. A handle 2076 in the form of a disc is provided, although other shaped handles are also contemplated. Shaft 2075 is preferably solid, but alternatively can have a lumen extending therethrough. The distal tip 2078 is configured to contact the proximalmost edge of the conduit portion 104 of the flow connector 100 to advance the flow connector from its loaded intermediate position (distal of the receiving area 2031 a) through the lumen 2017 of the delivery sheath 2012 and out the distal opening 2020.

Turning now to the method of use of the delivery system 2010, FIG. 10 illustrates the folding mechanism 2040 in the open position to enable loading of the flow connector 100 into the delivery sheath 2010. Note in these Figures, the flow connector 100 of FIG. 1D is shown, it being understood however that other flow connectors described herein, and the flow connectors described in U.S. Pat. No. 8,366,651, U.S.

patent publication 2009/0036820 and co-pending patent application Ser. No. 13/792,019, filed Mar. 9, 2013, incorporated herein in their entirety by reference, can be loaded into the instrument in the same manner. It should also be understood that the delivery system can be used to deliver other implants into the patient's body which can be loaded into the delivery sheath 2012.

With the folding mechanism 2040 in the open position, the flow connector 100 is placed through the axial slot 2026a in the handle tube 2027 and seated in the receiving area 2031a of handle tube 2027 as shown in FIG. 10. Note in this position the load plunger 2050 is in the retracted position and the deployment plunger 2070 is not yet utilized and remains separate from the device. In this inserted (placement) position, flange 102 of the flow connector extends through both slots 2026a and 2026b in handle tube 2027 of the delivery sheath 2012. Note that the flow connector is preferably loaded so that the shorter rounded flange region (toe portion) 102a is angled toward the distal portion of the delivery sheath 2012 and extends through slot 2026a and the longer flange region (heel portion) 102b is directed toward the proximal portion and extends through slot 2026b. Note further that when the flow connector is seated in the receiving area 2031a, the flange 102 extends outside the receiving area. That is, as loaded, the flange extends beyond the outer diameter of the outer wall of the delivery sheath 2012. This enables a reduced dimension sheath to be utilized since the lumens 2031 and 2017 of the delivery sheath 2012 can be sized to receive the conduit portion of the flow connector, which has a smaller transverse dimension than the flange.

After proper placement within the delivery sheath 2012, the folding mechanism 2040 is pivoted to a closed position as shown in FIG. 11. Such movement moves the folding block 2046 toward the flow connector and into contact with the conduit portion 104 of the flow connector 100, to compress a middle portion of the conduit portion 104 to fold it to a U-shaped configuration, best shown in FIG. 14. In one embodiment, the length of the folding block 2046 can be substantially the same length as the conduit portion of the flow connector, although other lengths are also contemplated.

Once the folding block 2046 is pivoted to a closed position, the load plunger 2050 is advanced through lumen 2031 of handle tube 2027 of the delivery sheath 2012 to the position of FIG. 12, thereby advancing the flow connector 100 distal of the receiving area 2031a and into the lumen 2017 to a "loaded position", distal of axial slots 2026a, 2026b at the distal edge forces the flow connector 100 distally. Deployment plunger 2070 can now be used. Note that as load plunger 2050 is advanced, distal slot 2056 enables the load plunger 2050 to slide past folding block 2046 and proximal slot 2058 slides along fixed pin 2055. Also note that with such folding of the conduit portion 104 when the flow connector 100 is advanced, the heel portion 102b is positioned alongside, i.e., substantially longitudinally aligned with, an outer wall of the flow connector and the toe portion 102a points in a distal direction and extends distally of the heel portion (see FIG. 15).

Folding mechanism 2040 is then opened, at least moved a sufficient distance so the folding pin 2046 is out of the receiving area 2031a to make room for advancement of the deployment plunger 2070. Deployment plunger 2070 is then inserted through the bore 2057 in load plunger 2050 and through the lumen 2059 to the position of FIG. 13. In an alternate embodiment, instead of the user manually moving the folding mechanism 2040 to enable advancement of the deployment plunger 2070, the deployment plunger is configured to contact and pivot the folding block out of the way to enable advancement of the deployment plunger.

Figure 16A:
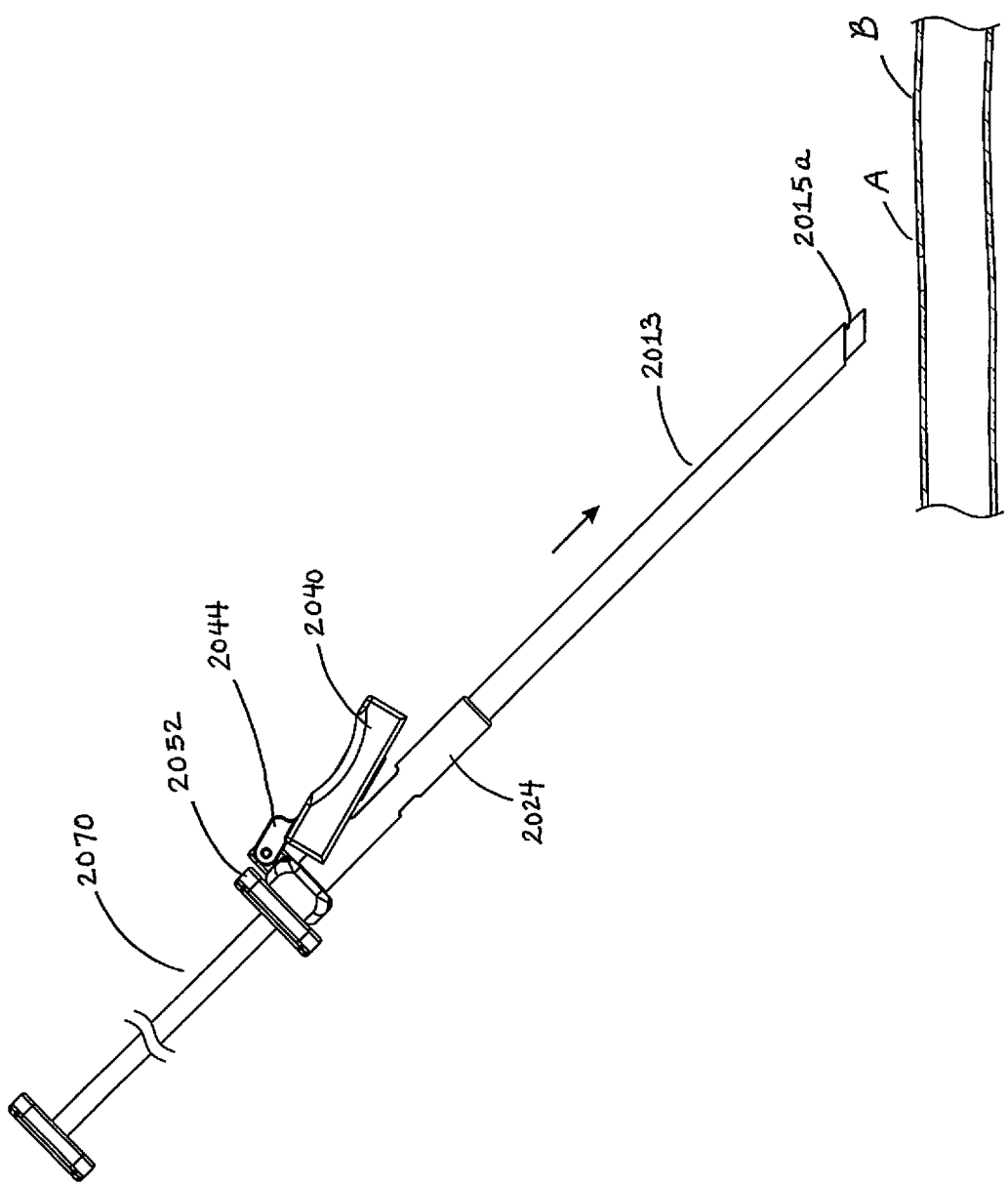

The delivery sheath 2012 with inserted deployment plunger 2070 is then inserted through the opening A (FIG. 16A) in the first body space, e.g., a source element such as an artery, designated by reference "B", as shown in FIG. 16B. Note it is inserted until stop 2015a contacts the outer wall C of the artery B. The distal tip of the delivery sheath 2012 is positioned so that the distal opening 2020 is in the lumen D of the artery B. The deployment plunger 2070 is then advanced distally into lumen 2017 of delivery tube 2013 so its distal end 2078 contacts a proximalmost end of the conduit portion 104 of the flow connector 100. Full advancement of the plunger 2070 can then be effected to advance the flow connector 100 out the distal opening 2020 of the delivery sheath 2012 into the artery B.

Figure 17:
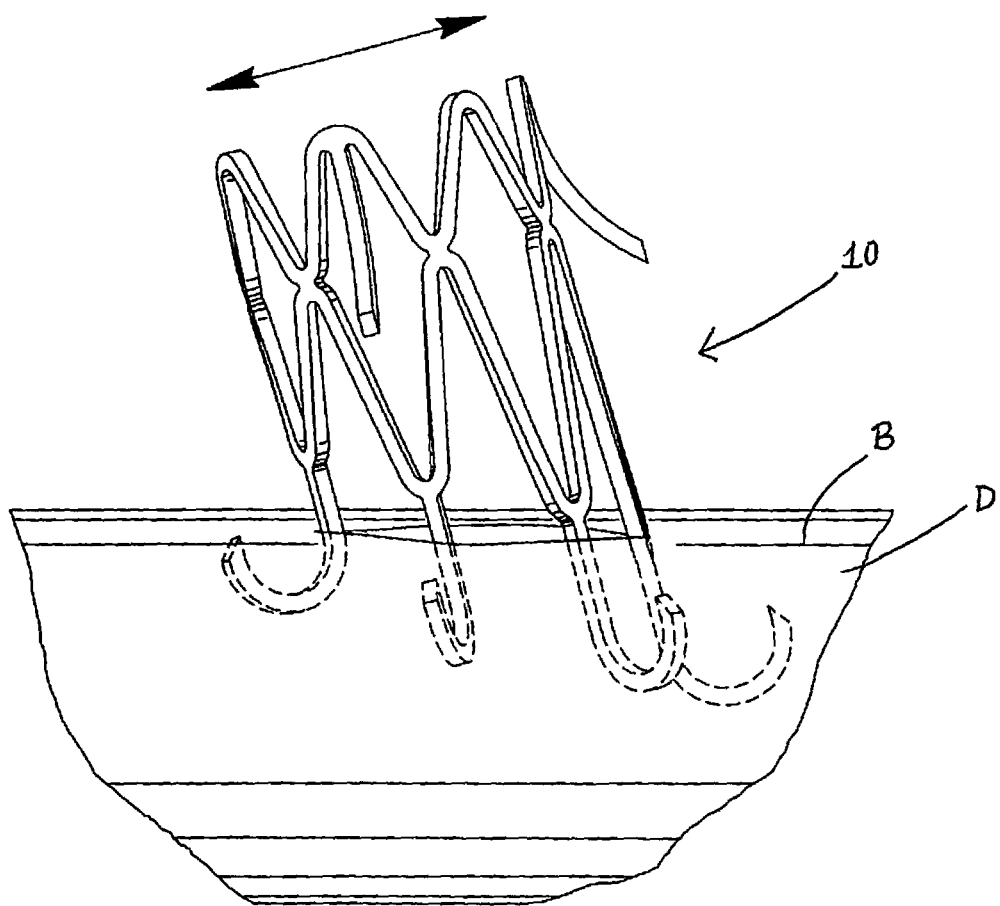
FIG. 17 illustrates one embodiment of a retention element positioned in the artery for receipt of the delivery system therethrough.

It should be appreciated that if the flow connector is used in conjunction with a retention device, such as the retention device disclosed in co-pending application Ser. No. 13/792,019, the entire contents of which are incorporated herein by reference, the delivery sheath 2012 would be inserted through the retention device. An example of such retention device is illustrated in FIG. 17 and designated by reference numeral 10. The delivery system 2010 would thus be inserted through the retention device 10 into the lumen D of artery B to deliver the flow connector in the manner described herein.

Figure 16C:
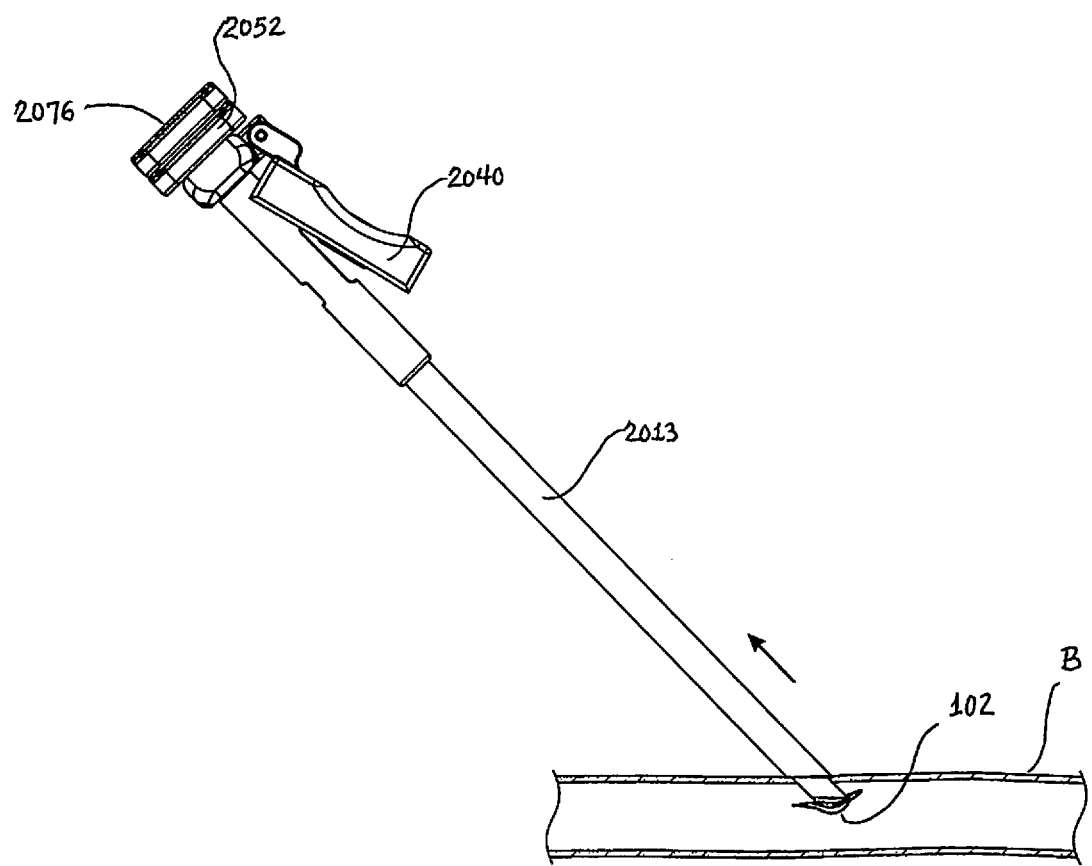
Figure 16D:
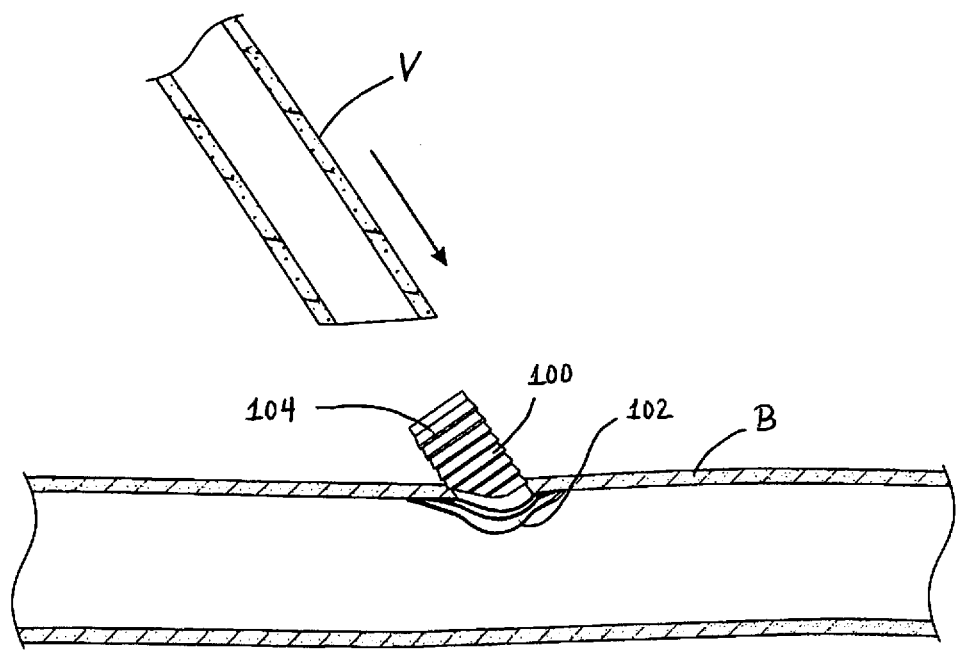
Figure 16E:
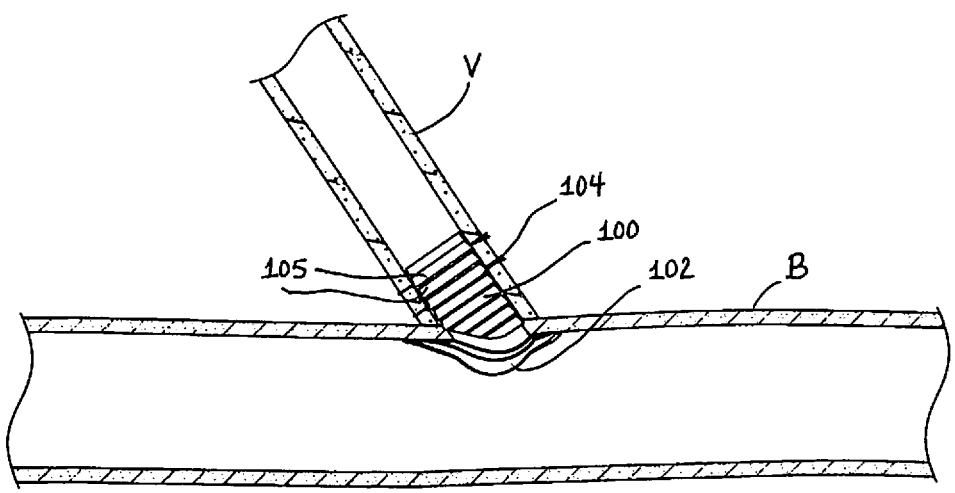

After the distal tip of the delivery sheath 2010 is in the desired position, the delivery plunger 2070 is fully advanced to move the flow connector 100 through the lumen 2017 of delivery sheath 2012 and out the distal opening 2020 as the distal edge forces the flow connector 100 distally. After delivery of the flow connector 100 to the artery B, (FIG. 16C) the delivery sheath 2010 and plunger 2070 are withdrawn, leaving the flow connector in position in the artery B as shown in FIG. 16D. A vein V is then advanced over the conduit portion 104 of the flow connector 100, and sutures or alternatively a band are placed around the outside of the vein V and positioned around the protrusions 105 of the conduit portion 104, thereby retaining the flow connector 100 in position to create a fluid tight end to side anastomosis.

It should be appreciated that the deployment plunger 2070, being a separate component, can be packaged as a kit with the delivery sheath 2012. The kit can also include one or more flow connectors or the flow connectors can be packaged separately.

FIGS. 18-23 illustrate an alternate embodiment of a delivery system of the present invention, designated generally by reference numeral 3010. Delivery system 3010 differs from delivery system 2010 in that the deployment plunger is attached to the delivery sheath and is not a separate component.

More specifically, delivery system 3010, like delivery system 2010, has a delivery sheath 3012 with a handle 3024, an implant receiving area in the handle tube 3027 and a lumen in the delivery sheath. The delivery sheath 3012 is identical to delivery sheath 2012 of FIGS. 8-16 and therefore is not discussed in further detail. Folding mechanism 3040 is also identical to folding mechanism 2040 of FIGS. 8-16 and therefore further discussion is not provided since the components and function are identical to folding mechanism 2040.

Load plunger 3050 is identical to load plunger 2050 except for the bore 3064 at the proximal end. The load plunger 3050 is configured to advance the flow connector 100 from the initial position in the receiving area of the delivery sheath 3012 to a predeployed or load position distal of the receiving area in the lumen of the delivery tube of the delivery sheath 3012 in the same manner as load plunger 2050 discussed above. That is, like load plunger 2050, load plunger 3050 has a disc shaped handle 3052 (although other shaped handles are also contemplated), a shaft with opposing axial slots formed in the wall through which the flange of the flow connector extends, and a lumen extending through the shaft and handle 3052. The shaft has a distal edge like distal edge 2053 of shaft 2054 to contact a proximal portion of the conduit portion of the flow connector 100. The bore 3064 at the proximal end leads into the lumen to enable advancement of the delivery plunger 3070 through the lumen of the load plunger 3050, the lumen of the handle tube 3027 and the lumen of the delivery sheath 3012 to deploy the flow connector from the delivery sheath 3012. However, the bore 3064, due to its configuration, also blocks advancement of the deployment plunger 3070.

More specifically, bore 3064 has a first dimension D1 (FIG. 23) and a second dimension D2 transverse to the first dimension and smaller than the first dimension. In the illustrated embodiment, the bore 3064 is slightly oval in configuration, although other configurations are also contemplated.

Deployment plunger 3070 differs from deployment plunger 2070 in that it is attached to the delivery sheath and is not a separate component. Deployment plunger 3070 also has a different cross-sectional dimension that the deployment plunger 2070. More specifically, proximal shaft portion 3075 is substantially oval or substantially D-shaped in cross section and distal shaft portion 3079 is substantially circular in configuration, with a reduced diameter intermediate portion 3077 between the shaft portions 3075, 3079 (see FIGS. 22 and 23). Deployment plunger has a handle 3076 in the form of a disc, although other shaped handles are also contemplated. The shaft is preferably solid, but alternatively can have a lumen extending therethrough. The distal edge of the plunger 3070 is configured to contact the conduit portion 104 of the flow connector to advance the flow connector from its loaded intermediate position (distal of the receiving area) through the lumen of the delivery sheath 3012 and out the distal opening in the same manner as deployment plunger 2070 explained in detail above.

Figure 18:
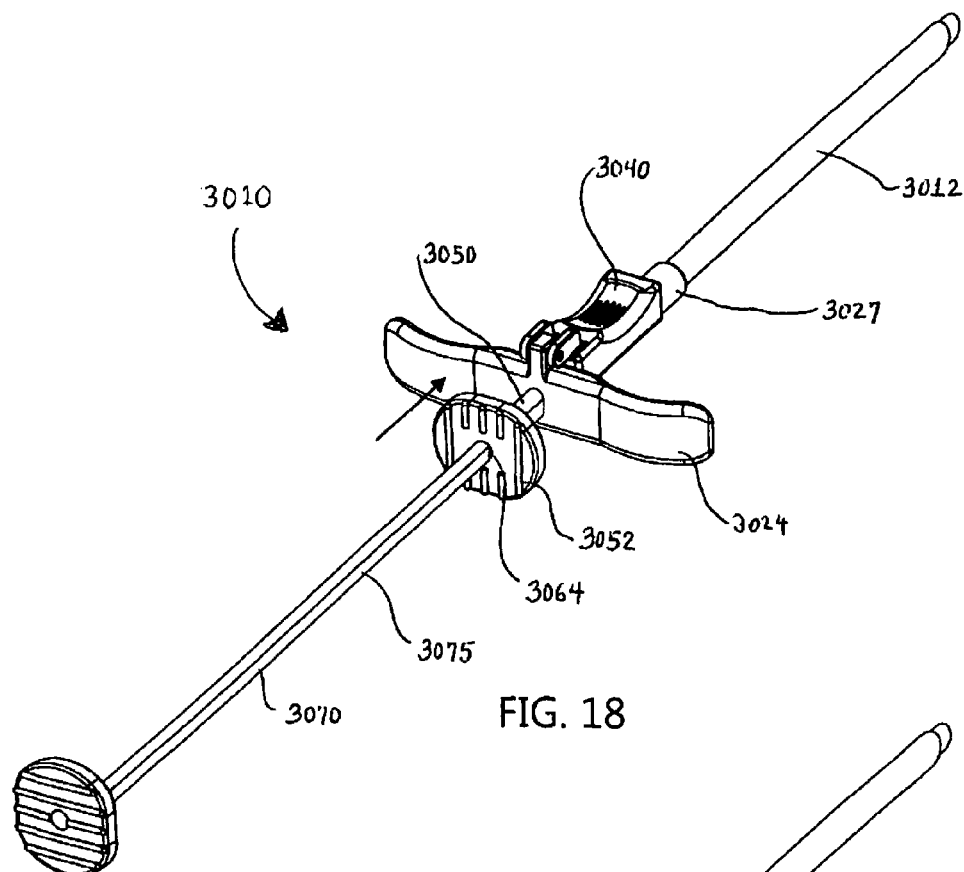
FIG. 18 is a perspective view of an alternate embodiment of the delivery system of the present invention showing the load plunger and delivery plunger in the retracted position, and showing the folding mechanism in the closed position.
Figure 19:
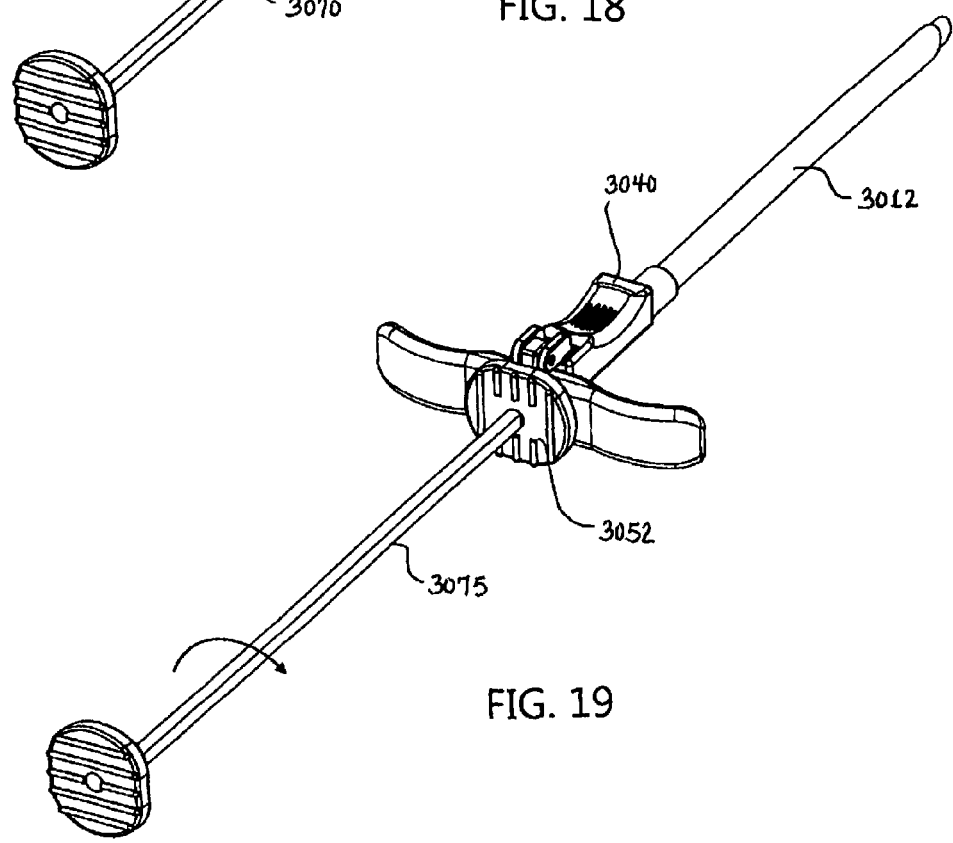
FIG. 19 is a view similar to FIG. 18 illustrating the load plunger in the advanced position and the direction of rotation of the delivery plunger.
Figure 20:
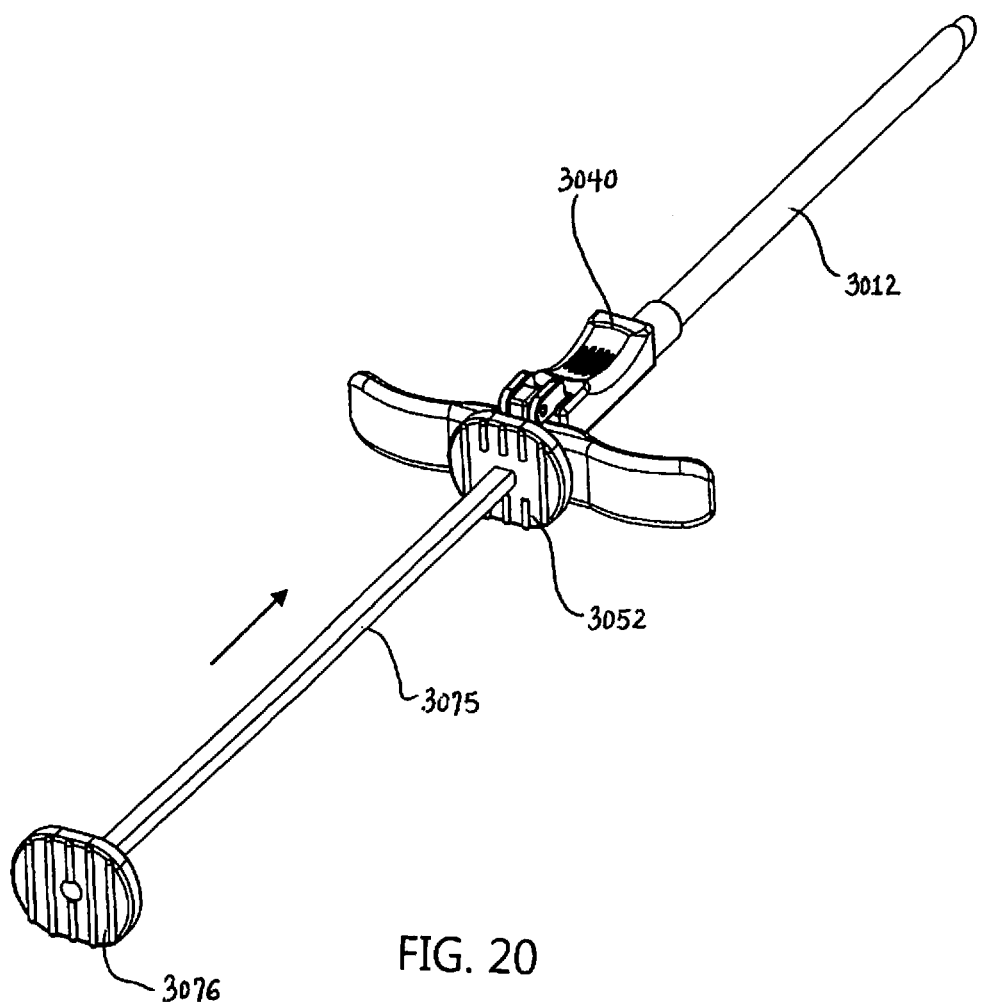
FIG. 20 is a view similar to FIG. 19 illustrating the delivery plunger rotated to a delivery position.
Figure 21:
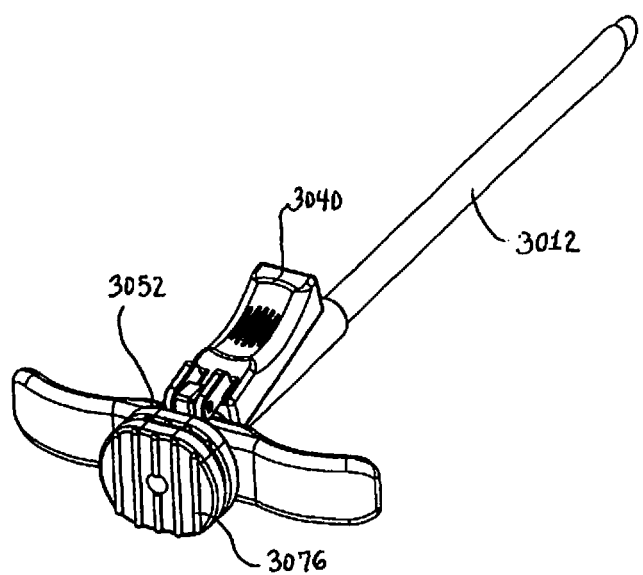
FIG. 21 is a view similar to FIG. 20 illustrating the delivery plunger in an advanced position.

Deployment plunger 3070 also differs from deployment plunger 2070 in that it is rotated from a first position to a second position to perform its deployment function. More specifically, as shown in FIG. 18, deployment plunger 3070 is in a first position wherein it cannot be inserted through bore 3064 of load plunger 3050 because its cross-sectional dimension exceeds dimension D2 of bore 3064. That is, the height h of the deployment plunger 3070 is greater that the dimension D2 of bore 3064 so it cannot fit through the bore as shown in FIGS. 18, 19, 22 and 23. In this first position, to advance the load plunger 3050, plunger 3070 is advanced as the edge 3075a of shaft portion 3075 abuts the area of handle 3052 adjacent bore 3064. Note it is also contemplated that the user can alternatively advance the load plunger 3050 by pressing the handle 3052. Once the load plunger 3050 is advanced to move the flow connector 100 out of the receiving area and into the lumen of delivery tube 3012 to its loaded position, the user can now advance the flow connector 100 from the delivery sheath 3012. To achieve this, the delivery plunger is rotated about 90 degrees from the position of FIG. 19 to the position of FIG. 20 so its width w is aligned with the dimension D2 of bore 3064 and height h is aligned with dimension D1. Since the width w is less than dimension D2 and the height h is less than dimension D1, the user can then advance the delivery plunger 3070 through the lumen in the load plunger 3050 to contact and advance the flow connector through the lumen of the delivery sheath 3012.

The method of use will now be described. The flow connector (or any of the aforementioned flow connectors) is loaded into the delivery sheath 3012 in the same manner as in the embodiment of FIGS. 8-11, i.e., the flow connector is inserted through the slot in the load plunger and seated in the receiving area with the flange of the flow connector extending beyond the outer diameter of the handle tube 3027. Next, the folding mechanism 3040 is closed to deform, e.g., fold, the flow connector. The load plunger 3050 is then advanced to move the flow connector distally from the receiving area further into the lumen of the delivery tube. The folding mechanism 3040 is then moved out of its closed position and the delivery system is advanced through the first body space, e.g., a source element such as an artery, in the same manner as in FIGS. 16A and 16B. The deployment plunger 3070 is then rotated to the position of FIG. 20 and advanced through the delivery sheath 3012 to deploy the flow connector through the distal opening of the delivery sheath, and then the delivery system is withdrawn in the same manner as shown in FIGS. 16C and 16D. A second body space, e.g., a destination element such as a vein, is then placed over the flow connector as in FIGS. 16D and 16E.

Note that in alternative embodiments, the delivery system of the present invention can be used to deliver multiple implants sequentially. For example, after the load plunger is advanced to advance the implant from the receiving area of the handle tube, the folding mechanism can be opened and the load plunger retracted to load another implant into the receiving area. The folding mechanism can then be closed to deform the implant and the load plunger can then be re-advanced to move the implant out of the receiving area which would contact the implant in the lumen of the delivery tube and move it forward. In this manner, the load plunger can be retracted and re-advanced multiple times, stacking the implants along an axis of the delivery tube lumen. The deployment plunger can then be advanced incrementally to deploy each implant by pressing on the proximalmost implant to move the whole row forward.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

The invention claimed is:

1. A method for delivering an implantable flow connector to a first space within the body of a patient to couple the first space within the body to a second space within the body, the flow connector having a conduit with a lumen terminating at an orifice at opposing first and second ends of the conduit, wherein a second end of the conduit is configured to be implanted in the second space within the body, the method comprising the steps of:

providing a delivery member having a lumen and a receiving area at a proximal portion of the delivery member remaining outside the body of the patient;

placing the flow connector within the receiving area;

moving a deforming member from a first position to a second position to press the conduit portion of the flow connector to deform the flow connector to reduce its profile at the proximal portion of the delivery member; and delivering the flow connector through the lumen of the delivery member into the first body space, wherein the flow connector includes a flange radially extending from the conduit, and the step of delivering the implant to the first body space places the flange within the first body space, and the step of moving the deforming member to the second position causes a folding block of the deforming member to move closer toward a longitudinal axis of the delivery member to press the conduit of the flow connector without contact with the flange to thereby fold the conduit into a U-shaped cross-sectional configuration.

2. The method of claim 1, wherein when the flow connector is placed within the receiving area, the flange of the flow connector extends beyond an outer wall of the delivery member at the proximal portion of the delivery member.

3. The method of claim 1, wherein the first space within the body is a source element and the second space within the body is a destination element.

4. The method of claim 1, wherein the step of delivering the flow connector through the lumen of the delivery member comprises the steps of advancing a first plunger to move the flow connector from the receiving area to an intermediate position within the lumen of the delivery member and subsequently advancing a second plunger to deliver the flow connector out a distal opening of the delivery member.

\* \* \* \* \*